(12) United States Patent
Sharma et al.

(10) Patent No.: US 7,795,378 B2
(45) Date of Patent: Sep. 14, 2010

(54) PEPTIDE COMPOSITIONS FOR TREATMENT OF SEXUAL DYSFUNCTION

(75) Inventors: Shubh D. Sharma, Cranbury, NJ (US); Annette M. Shadiack, Somerset, NJ (US); Ramesh Rajpurohit, Hillsboro, NJ (US); Wei Yang, Edison, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 1276 days.

(21) Appl. No.: 11/031,898

(22) Filed: Jan. 7, 2005

(65) Prior Publication Data

US 2005/0124553 A1 Jun. 9, 2005

Related U.S. Application Data

(63) Continuation-in-part of application No. PCT/US03/21417, filed on Jul. 9, 2003.

(60) Provisional application No. 60/394,756, filed on Jul. 9, 2002.

(51) Int. Cl.
*A61K 38/00* (2006.01)
*A61K 31/56* (2006.01)
*C07K 4/00* (2006.01)
*C07K 5/00* (2006.01)
*C07K 7/00* (2006.01)
*C07K 14/00* (2006.01)
*C07K 17/00* (2006.01)
*A61K 51/00* (2006.01)

(52) U.S. Cl. ........................... 530/300; 514/180; 514/2; 424/1.69

(58) Field of Classification Search ................. 514/180
See application file for complete search history.

(56) References Cited

U.S. PATENT DOCUMENTS

| | | | |
|---|---|---|---|
| 5,576,290 | A | 11/1996 | Hadley |
| 5,674,839 | A | 10/1997 | Hruby et al. |
| 5,693,608 | A | 12/1997 | Bechgaard et al. |
| 5,714,576 | A | 2/1998 | Hruby et al. |
| 5,908,825 | A | 6/1999 | Fasano et al. |
| 5,977,070 | A | 11/1999 | Piazza et al. |
| 6,051,555 | A | 4/2000 | Hadley |
| 6,284,729 | B1 | 9/2001 | Bernfield et al. |
| 6,350,760 | B1 | 2/2002 | Bakshi et al. |
| 6,376,509 | B1 | 4/2002 | Bakshi et al. |
| 6,410,548 | B2 | 6/2002 | Nargund et al. |
| 6,458,790 | B2 | 10/2002 | Palucki et al. |
| 6,472,398 | B1 | 10/2002 | Palucki et al. |
| 6,534,503 | B1 | 3/2003 | Dines et al. |
| 6,579,968 | B1 | 6/2003 | Blood et al. |
| 2001/0056179 | A1 | 12/2001 | Chen et al. |
| 2002/0004512 | A1 | 1/2002 | Bakshi et al. |
| 2002/0137664 | A1 | 9/2002 | Bakshi et al. |
| 2002/0143141 | A1 | 10/2002 | Chen et al. |
| 2003/0069169 | A1 | 4/2003 | Macor et al. |
| 2004/0077540 | A1 * | 4/2004 | Quay ........................... 514/12 |

FOREIGN PATENT DOCUMENTS

| | | |
|---|---|---|
| WO | WO 99/55679 | 11/1999 |
| WO | WO 99/64002 | 12/1999 |
| WO | WO 00/53148 | 9/2000 |
| WO | WO 00/74679 | 12/2000 |
| WO | WO 01/00224 | 1/2001 |
| WO | WO 01/05401 | 1/2001 |
| WO | WO 01/10842 | 2/2001 |
| WO | WO 02/18437 | 3/2002 |
| WO | WO 2004/005324 | 1/2004 |

OTHER PUBLICATIONS

Benelli A, Poggioli R, Luppi P, Ruini L, Bertolini A, Arletti R., Oxytocin enhances, and oxytocin antagonism decreases, sexual receptivity in intact female rats. *Neuropeptides* 27:245-50 (1994).

Wessells H. et al., *J Urology* 160:389-393 (1998).

Vergoni, A. V.; Bertolini, A.; Guidetti, G.; Karefilakis, V.; Filaferro, M.; Wikberg, J. E.; Schioth, H. B., Chronic melanocortin 4 receptor blockage causes obesity without influencing sexual behavior in male rats. *J Endocrinol* 166:419-26 (2000).

See generally *Synthetic Peptides: A User's Guide*, GA Grant, editor, W.H. Freeman & Co., New York (1992), the teachings of which are incorporated herein by reference, including the text and table set forth at pp. 11 through 24.

Hruby V.J., Al-obeidi F. and Kazmierski W., Emerging approaches in the molecular design of receptor-selective peptide ligands—conformational, topographical and dynamic considerations. *Biochem J* 268:249-262 (1990).

(Continued)

*Primary Examiner*—Maury Audet
(74) *Attorney, Agent, or Firm*—Stephen A. Slusher

(57) ABSTRACT

A peptide of the structural formula:

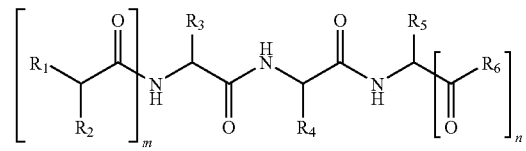

or a pharmaceutically acceptable salt thereof, wherein $R_1$, $R_2$, $R_3$, $R_4$, $R_5$, $R_6$, m and n are as defined. Further provided are methods for treatment of sexual dysfunction, including erectile dysfunction and female sexual dysfunction, and combination drugs and method of use thereof, including a peptide of the invention and one or more second sexual dysfunction pharmaceutical agents.

4 Claims, 1 Drawing Sheet

OTHER PUBLICATIONS

Toniolo C., Conformationally restricted peptides through short-range cyclizations. *Int J Peptide Protein Res* 35:287-300 (1990).

*Angew Chem* 24:799-810 (1985) and Barany et al., *The Peptides, Analysis, Synthesis and Biology*, vol. 2,.Gross, E. and Meienhofer, J., Eds. Academic Press 1-284 (1980).

M.E. Hadley et al., Discovery and development of the novel melanogenic drugs, in *Integration of Pharmaceutical Discovery and Development: Case Studies*, edited by Borschart et al., Plenum Press, New York (1998).

R.T. Dorr et al., Evaluation of Melanotan-II, A Superpotent Cyclic Melanotropic Peptide in a Pilot Phase-I Clinical Study. *Life Sci* 58:1777-1784 (1996).

R.A.H. Adan, Identification of Antagonists for Melanocortin MC3, MC4, and MC5 Receptors. *EurJ Pharmacol*, 269:331-337 (1994).

Hruby V.J., Lu D., Sharma S.D., et al. Cyclic lactam alpha-melanotropin analogues of Ac-Nle$^4$-cyclo[Asp$^5$, D-Phe$^7$, Lys$^{10}$]NH$_2$ with bulky aromatic amino acids at position 7 show high antagonist potency and selectivity at specific melanocortin receptors. *J Med Chem* 38:3454-3461 (1995).

* cited by examiner

SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: alpha-melanocyte stimulating hormone
      tetrapeptide core sequence

<400> SEQUENCE: 1

His Phe Arg Trp
1

PEPTIDE COMPOSITIONS FOR TREATMENT OF SEXUAL DYSFUNCTION

CROSS-REFERENCE TO RELATED APPLICATIONS

This application is a continuation-in-part application of International Application PCT/US03/21417, entitled Peptide Compositions for Treatment of Sexual Dysfunction, filed on Jul. 9, 2003, and claims the benefit of the filing of U.S. Provisional Patent Application Ser. No. 60/394,756, entitled Compositions for Treatment of Sexual Dysfunction, filed on Jul. 9, 2002. The specification of each is incorporated herein by reference.

BACKGROUND OF THE INVENTION

1. Field of the Invention (Technical Field)

The present invention relates to peptides and pharmaceutical compositions including peptides for the treatment of sexual dysfunction in mammals, including both male erectile dysfunction and female sexual dysfunction in humans, including methods and formulations for the use and administration of the same.

2. Description of Related Art

Note that the following discussion refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

Sexual dysfunction, including both penile erectile dysfunction or impotence and female sexual dysfunction, is a common medical problem. Significant effort has been devoted over the last twenty or more years to develop methods, devices and compounds for treatment of sexual dysfunction. While more effort has been undertaken for treatment of penile erectile dysfunction, female sexual dysfunction is also an area to which significant research and effort has been devoted.

At present, one commonly used orally administered drug for treatment of sexual dysfunction in the male is Viagra®, a brand of sildenafil, which is a phosphodiesterase 5 (PDE-5) inhibitor. PDE-5 inhibitors increase the persistence of cyclic guanosine monophosphate and thereby enhance erectile response. Another drug approved in Europe for treating male erectile dysfunction is Ixense®, a brand of apomorphin that is a non-selective dopa receptor agonist. Oral and nasal formulations of apomorphin are currently undergoing clinical evaluations in the United States. There are several other medical treatment alternatives currently available depending on the nature and cause of the impotence problem. Some men have abnormally low levels of the male hormone testosterone, and treatment with testosterone injections or pills may be beneficial. However, comparatively few impotent men have low testosterone levels. For many forms of erectile dysfunction, treatment may be undertaken with drugs injected directly into the penis, including drugs such as papaverin, prostaglandin $E_1$, phenoxybenzamine or phentolamine. These all work primarily by dilating the arterial blood vessels and decreasing the venous drainage. Urethral inserts, such as with suppositories containing prostaglandin, may also be employed. In addition, a variety of mechanical aids are employed, including constriction devices and penile implants.

A variety of treatments have also been explored for female sexual dysfunction, including use of sildenafil, although the Food and Drug Administration has not specifically approved such use. Testosterone propionate and various estrogen-related compounds have also been employed to increase or augment female libido.

A number of other agents have been shown to induce or facilitate penile erection in laboratory animals. These include very diverse classes of ligands such as oxytocin (Benelli A, Poggioli R, Luppi P, Ruini L, Bertolini A, Arletti R., Oxytocin enhances, and oxytocin antagonism decreases, sexual receptivity in intact female rats. *Neuropeptides* 27:245-50 (1994)), vasopressin, vasoactive intestinal peptide, melanotropins, and ACTH as well as their analogs.

It is well known to those skilled in the art of developing new therapeutic treatments for sexual dysfunction that identification of a new class of therapeutic agents is often achieved by chance. For example, investigations of sildenafil as an agent for treating high blood pressure in humans revealed its effects on facilitating penile erection in men. Similarly, clinical use of apomorphin for treatment of Parkinson's disease uncovered its effects in eliciting penile erections. Human studies on a potent melanotropin agonist as an agent to induce human skin pigmentation established its erectogenic activity. However, the mechanism by which these agents elicit a sexual activity response remains largely unknown. Some understanding of the PDE-5 class of compounds (e.g. sildenafil) has now been developed. The biological mechanism(s) by which presumably centrally acting molecules, such as oxytocin, vasopressin, apomorphin, vasoactive intestinal peptide, melanotropins and ACTH, elicit a sexual function response is still unclear. That at least a portion of the biological mechanism is central is generally understood to be demonstrated by efficacy following intracerebroventricular (ICV) administration. It is conceivable that some or all of these agents may be interacting at more than one individual receptor site involved in a common downstream biological pathway.

Melanocortin receptor-specific compounds have been explored for use of treatment of sexual dysfunction. In one report, a cyclic α-melanocyte-stimulating hormone ("α-MSH") analog, called Melanotan-II, was evaluated for erectogenic properties for treatment of men with psychogenic erectile dysfunction. Wessells H. et al., *J Urology* 160:389-393 (1998); see also U.S. Pat. No. 5,576,290, issued Nov. 19, 1996 to M. E. Hadley, entitled Compositions and Methods for the Diagnosis and Treatment of Psychogenic Erectile Dysfunction and U.S. Pat. No. 6,051,555, issued Apr. 18, 2000, also to M. E. Hadley, entitled Stimulating Sexual Response in Females. A related compound is claimed in U.S. Pat. No. 6,579,968, Compositions and Methods for Treatment of Sexual Dysfunction, issued Jun. 17, 2003, to C. H. Blood and others, and is in clinical trials for treatment of erectile dysfunction. The peptides used in U.S. Pat. Nos. 5,576,290 and 6,051,555 are also described in U.S. Pat. No. 5,674,839, issued Oct. 7, 1997, to V. J. Hruby, M. E. Hadley and F. Al-Obeidi, entitled Cyclic Analogs of Alpha-MSH Fragments, and in U.S. Pat. No. 5,714,576, issued Feb. 3, 1998, to V. J. Hruby, M. E. Hadley and F. Al-Obeidi, entitled Linear Analogs of Alpha-MSH Fragments. Additional related peptides are disclosed in U.S. Pat. Nos. 5,576,290, 5,674,839, 5,714,576 and 6,051,555. These peptides are described as being useful for both the diagnosis and treatment of psychogenic sexual dysfunction in males and females. Other peptides are disclosed in U.S. Pat. No. 6,284,735 and U.S. Published Patent Applications Nos. 2001/0056179 and 2002/0004512.

It has long been believed that erectile response to melanocortin receptor-specific compounds, and both male and female sexual response in general, was related to the central tetrapeptide sequence, His⁶-Phe⁷-Arg⁸-Trp⁹ (SEQ ID NO:1) of native α-MSH. In general, all melanocortin peptides share the same active core sequence, His-Phe-Arg-Trp (SEQ ID NO:1), including melanotropin neuropeptides and adrenocorticotropin. MC3-R (the melanocortin-3 receptor) has the highest expression in the arcuate nucleus of the hypothalamus, while MC4-R (the melanocortin-4 receptor) is more widely expressed in the thalamus, hypothalamus and hippocampus. A central nervous system mechanism for melanocortins in the induction of penile erection has been suggested by experiments demonstrating penile erection resulting from central intracerebroventricular administration of melanocortins in rats. While the mechanism of His-Phe-Arg-Trp (SEQ ID NO:1) induction of erectile response has never been fully elucidated, it has been generally accepted that the response involves the central nervous system, and binding to MC3-R and/or MC4-R, and according to most researchers, MC4-R.

Non-peptides have been proposed which alter or regulate the activity of one or more melanocortin receptors. For example, International Patent Application No. PCT/US99/09216, entitled Isoquinoline Compound Melanocortin Receptor Ligands and Methods of Using Same, discloses two compounds that induce penile erections in rats. However, these compounds were administered by injection at doses of 1.8 mg/kg and 3.6 mg/kg, respectively, and at least one compound resulted in observable side effects, including yawning and stretching. Other melanocortin receptor-specific compounds with claimed application for treatment of sexual dysfunction are disclosed in International Patent Application No. PCT/US99/13252, entitled Spiropiperidine Derivatives as Melanocortin Receptor Agonists. International Patent Application Nos. PCT/US00/14930, PCT/US00/19408, WO 01/05401, WO/00/53148, WO 01/00224, WO 00/74679, WO 01/10842 and the like disclose other compounds that may be so utilized.

Most investigators, including those who are inventors of the above-described patents and applications, ascribe the sexual activity of melanotropin ligands to MC4-R. Evidence in favor of this hypothesis comes from the observation that a sexual response elicited by an MC4-R agonist can be blocked by an MC4-R antagonist. However, a few reports also suggest that MC4-R receptors may not be involved in eliciting sexual function response (Vergoni, A. V.; Bertolini, A.; Guidetti, G.; Karefilakis, V.; Filaferro, M.; Wikberg, J. E.; Schioth, H. B., Chronic melanocortin 4 receptor blockage causes obesity without influencing sexual behavior in male rats. *J Endocrinol* 166:419-26 (2000)).

BRIEF SUMMARY OF THE INVENTION

In one embodiment the invention provides a peptide of structural formula I:

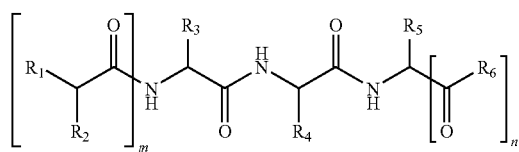

I or a pharmaceutically acceptable salt thereof.

In peptides of formula I. $R_1$ is $NH_2$, $NH_3^+$, $NH_2$—$R_7$, or H. $R_2$ is H or a linear or branched $C_1$ to $C_{17}$ alkyl, aryl, heteroaryl, alkene, alkenyl, or aralkyl chain. $R_2$ may thus include a $C_1$ to $C_{17}$ aliphatic linear or branched chain, an omega amino derivative of a $C_1$ to $C_{17}$ aliphatic linear or branched chain, or an acylated derivative of an omega amino derivative of a $C_1$ to $C_{17}$ aliphatic linear or branched chain.

$R_3$ and $R_4$ are independently a $C_1$ to $C_6$ aliphatic linear or branched chain, including $CH_3$, or an aromatic amino acid side chain moiety, on the proviso that not more than one of $R_3$ and $R_4$ is a $C_1$ to $C_6$ aliphatic linear or branched chain. In a preferred embodiment, both $R_3$ and $R_4$ are aromatic amino acid side chain moieties. Optionally the aromatic amino acid side chain moiety is derived from a natural or synthetic L- or D-amino acid, and is an aromatic substituted aryl or heteroaryl side chain. The aromatic ring or rings of the amino acid side chain moiety may be functionalized with one or more halogens or one or more alkyl or aryl groups. The aromatic amino acid side chain moiety is preferably selected from the following:

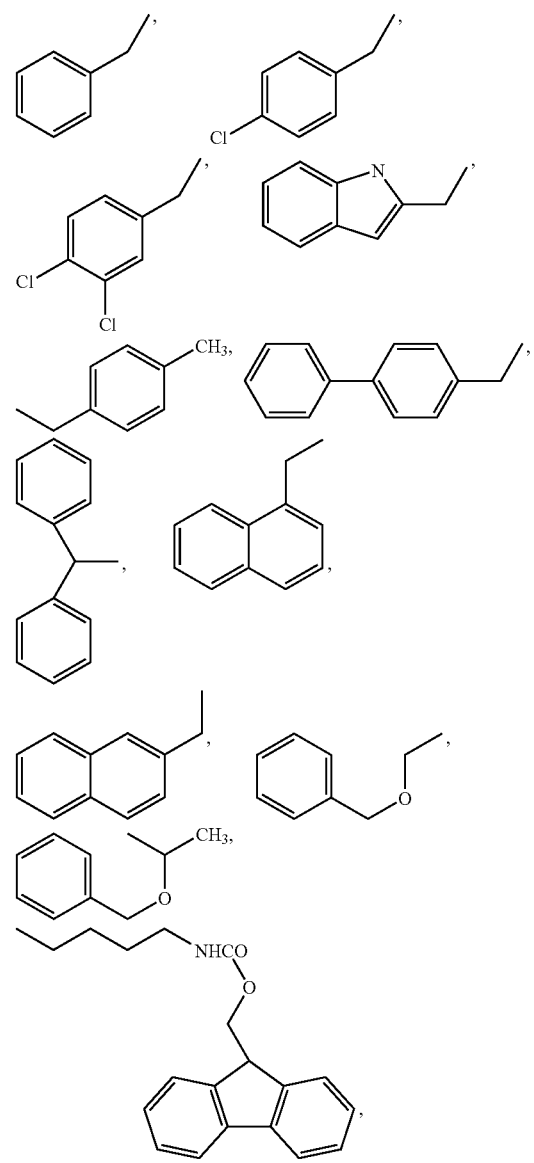

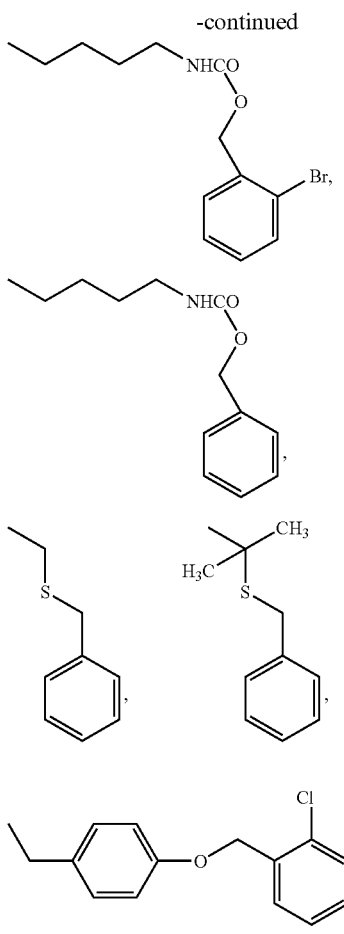

$R_5$ is a $C_1$ to $C_6$ linear or branched chain or a neutral hydrogen bonding or positively charged amino acid side chain moiety. Optionally the $C_1$ to $C_6$ linear or branched chain is $CH_3$. Optionally the neutral hydrogen bonding or positively charged amino acid side chain moiety is an aliphatic or aromatic amino acid side chain moiety derived from a natural or synthetic L- or D-amino acid, wherein the moiety includes at least one nitrogen-containing group, including an amide, imide, amine, guanidine, urea, urethane, or nitrile. The $R_5$ nitrogen-containing amino acid side chain moiety is preferably selected from the following:

The $R_5$ neutral aliphatic amino acid side chain moiety, wherein the side chain includes hydrogen donors and/or acceptors, is preferably selected from the following:

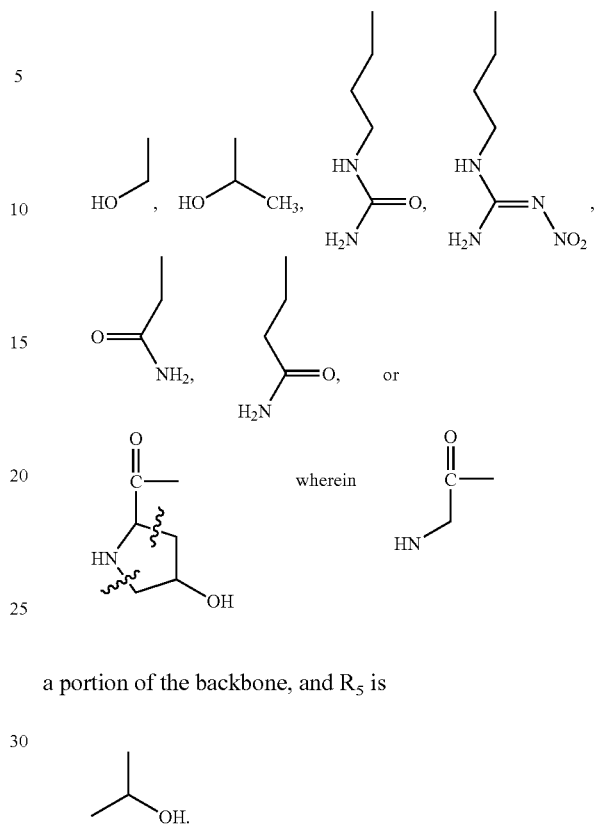

a portion of the backbone, and $R_5$ is $R_6$ is OH, $NH_2$, or NH—$R_7$. $R_7$ is a $C_1$-$C_{17}$ chain, including an alkyl, aryl, heteroaryl, alkene, alkenyl, or aralkyl. In the peptides of formula I, m is 0 or 1, on the proviso that if m is 0, then a single H occupies the position specified by m, such that the amino terminal group is $NH_2$. In the peptides of formula I, n is 0 or 1, on the proviso that if n is 0, then a single H occupies the position specified by n.

In an alternative embodiment, $R_5$ can be $R_5'$ and $R_5''$, such that the invention provides a peptide of structural formula II:

II or a pharmaceutically acceptable salt thereof.

In peptides of formula II, m, n, $R_1$, $R_2$, $R_3$, $R_4$, and $R_6$ are as defined for formula I, and at least one of $R_5'$ and $R_5''$ is as $R_5$ is defined for formula I, and the remaining of $R_5'$ or $R_5''$ is a lower aliphatic $C_1$-$C_4$ branched or linear alkyl chain, including methyl or ethyl.

Peptides of formula I or II contain one or more asymmetric centers and can thus occur as racemates and racemic mixtures, single enantiomers, diastereomeric mixtures and individual diastereomers. The present invention includes all such isomeric forms of the peptides of formula I and II. Certain of the peptides of formula I or II contain one or more alkenes, and thus contain olefinic double bonds, and formulas I and II are meant to include both E and Z geometric isomers where relevant. Other peptides of formula I or II may exist as tautomers, such as keto-enol tautomers. The individual tautomers as well as mixtures thereof are included with the definition of formulas I and II.

Peptides of formula I or II may be separated into their individual diastereoisomers by any means known in the art, including but not limited to fractional crystallization from a suitable solvent, such as methanol or ethyl acetate or a mixture thereof, or by chiral chromatography using an optically active stationary phase. It is also possible to synthesize a specific diastereoisomer of a peptide of formula I or II by stereospecific synthesis using optically pure starting materials or reagents of known configuration.

In a preferred embodiment, the peptides of formula I or II are synthesized using reagents of known configurations, and accordingly have a specific diastereoisomeric form.

The pharmaceutical compositions and peptides of the invention are characterized, in part, in that they do not bind to any significant degree, as determined by competitive inhibition assays utilizing radiolabeled α-MSH or analogs thereof, such as [$Nle^4$, D-$Phe^7$]-α-MSH (NDP-MSH), to any melanocortin receptor, including specifically MC1-R, MC3-R, MC4-R or MC5-R. Thus the pharmaceutical compositions and peptides exhibit neither agonist nor antagonist activity with respect to any of MC1-R, MC3-R, MC4-R or MC5-R. However, the pharmaceutical compositions and peptides do induce erectile activity in mammalian males, and may be employed for treatment of male sexual dysfunction, including erectile dysfunction, in mammalian males, and for female sexual dysfunction in mammalian females.

The invention thus further relates to peptides that are characterized in that they do not significantly bind MC4-R, or any other known melanocortin receptor, but which have some structural similarities to at least one molecular region of peptides that bind one or more melanocortin receptors, and specifically that bind MC4-R, and which further induce an erectile response in mammals. Thus the invention relates to peptides containing a His-D-Phe sequence, or alternatively containing a D-Phe-Arg sequence, or alternatively containing a His-D-Phe-Arg sequence, or a mimic or homolog of any of the foregoing, but which peptides of the invention do not bind to any melanocortin receptor, including specifically MC4-R. The peptides of the invention do not contain a Trp or mimic or homolog thereof, and thus are distinct from peptides or molecules that incorporate the His-Phe-Arg-Trp (SEQ ID NO:1) sequence or mimics or homologs thereof. The peptides of this invention induce erectile responses in a manner similar to agents described in prior art that bind MC4-R.

The invention further includes pharmaceutical compositions, including a peptide of this invention and a pharmaceutically acceptable carrier.

The invention further includes methods for treatment of sexual dysfunction, including treating erectile dysfunction in males or female sexual dysfunction, the methods including administration of a therapeutically effective amount of a peptide of this invention. In an alternative embodiment, the method further includes administration of the peptide in combination with a therapeutically effective amount of a second sexual dysfunction pharmaceutical agent. The second sexual dysfunction pharmaceutical agent can include an MC4-R agonist, which may be a peptide or a small molecule, a PDE-5 inhibitor, an alpha-andrenergic receptor antagonist, a sexual response related hormone, such as testosterone in males or estrogen in females, or other compounds or devices useful in treatment of sexual dysfunction. The present invention also encompasses pharmaceutical compositions useful in the foregoing method of the present invention, such as compositions including a peptide of formula I or II and one or more second sexual dysfunction pharmaceutical agents, as well as a method of manufacture of a medicament useful to treat sexual dysfunction.

The peptides of this invention, and pharmaceutical compositions of this invention, may be used for stimulating sexual response in a mammal. The invention thus also includes a method for stimulating sexual response in a mammal, in which a therapeutically effective amount of a pharmaceutical composition is administered. The mammal may be male or female. In this method, the composition can also include a pharmaceutically acceptable carrier. The peptide or pharmaceutical composition may be administered by any means known in the art, including administration by injection, administration through mucous membranes, buccal administration, oral administration, dermal administration, urethral administration, vaginal administration, inhalation administration and nasal administration. In a preferred embodiment, administration is by oral administration, including sublingual administration, of a specified amount of a formulation including an appropriate carrier, bulking agent and the like.

A first object of the present invention is to provide a pharmaceutical composition for use in treatment of sexual dysfunction wherein the active agent is not melanocortin receptor-specific.

A second object is to provide a peptide-based pharmaceutical for use in treatment of male sexual dysfunction, including erectile dysfunction, which is not melanocortin receptor-specific.

Yet another object is to provide a peptide-based pharmaceutical for use in treatment of female sexual dysfunction that is not melanocortin receptor-specific.

An advantage of the present invention is that it provides a peptide-based pharmaceutical for use in treatment of sexual dysfunction which may be administered by delivery systems other than art conventional intravenous, subcutaneous or intramuscular injection, including but not limited to oral delivery systems, nasal delivery systems and mucous membrane delivery systems.

Another advantage of the present invention is that it provides a peptide providing a sexual response similar to or superior to that of MC4-R specific agents, but without the side-effects or pharmacological responses unrelated to sexual response seen with MC4-R specific agents.

Other objects, advantages and novel features, and further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWING

The accompanying drawing, which is incorporated into and forms a part of the specification, illustrates an embodiment of the present invention and, together with the description, serves to explain a principle of the invention. The drawing is only for the purpose of illustrating a preferred embodiment of the invention and is not to be construed as limiting the invention.

DETAILED DESCRIPTION OF THE INVENTION

Definitions

Figure 1:
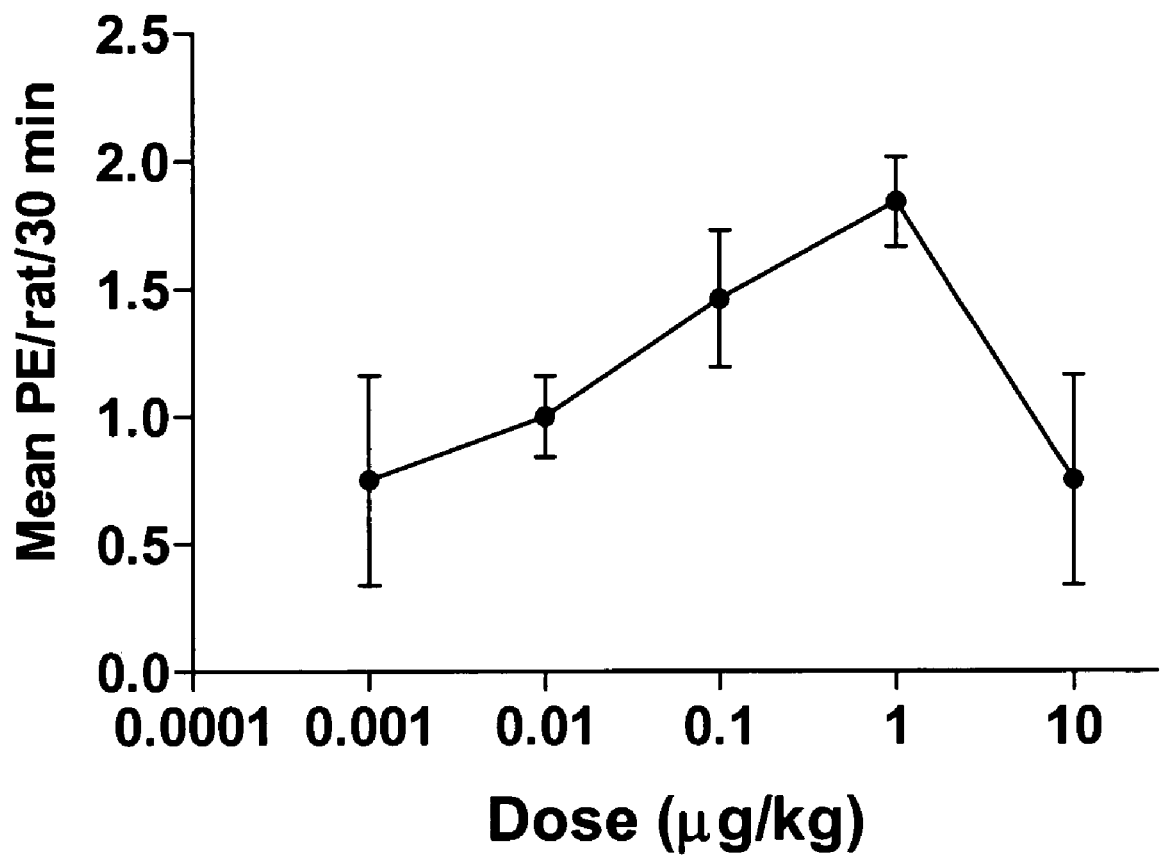
FIG. 1 is a dose response plot of mean penile erections per rat per 30 minute period following administration of varying doses of $NH_2$—$(CH_2)_6$—CO-Ser(Bzl)-D-Phe(4-Cl)-Arg ($NO_2$).

The "peptides" of this invention can be (a) naturally-occurring, (b) produced by chemical synthesis, (c) produced by recombinant DNA technology, (d) produced by biochemical or enzymatic fragmentation of larger molecules, (e) produced by methods resulting from a combination of methods (a) through (d), or (f produced by any other means for producing peptides.

By employing chemical synthesis, a preferred means of production, it is possible to introduce various amino acids which do not naturally occur along the chain, modify the N- or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino acids. For the most part, the peptides of this invention comprise fewer than 6 amino acids, and preferably ranging from about 3 to about 5 amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" includes structures that comprise one or more non-alpha-amino acid structures, such as for example aminoheptanoyl (as hereafter defined), in combination with two or more amino acids. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, a peptide made by any other method.

The term "amino acid side chain moiety" used in this invention, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition. A "derivative" of an amino acid side chain moiety is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties.

The "amino acids" used in this invention, and the term as used in the specification and claims, include the known naturally occurring protein amino acids, which are referred to by their common three letter abbreviation. See generally *Synthetic Peptides: A User's Guide*, G A Grant, editor, W.H. Freeman & Co., New York (1992), the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V. J., Al-obeidi F. and Kazmierski W., Emerging approaches in the molecular design of receptor-selective peptide ligands—conformational, topographical and dynamic considerations. *Biochem J* 268:249-262 (1990); and Toniolo C., Conformationally restricted peptides through short-range cyclizabons. *Int J Peptide Protein Res* 35:287-300 (1990); the teachings of all of which are incorporated herein by reference. In addition, the following abbreviations setting forth amino acids, constituent portions thereof, reagents used in synthesis thereof, and the like, have the meanings giving:

Abu—gamma-amino butyric acid
2-Abz—2-amino benzoic acid
3-Abz—3-amino benzoic acid
4-Abz—4-amino benzoic acid
Achc—1-amino-cyclohexane-1-carboxylic acid
Acpc—1-amino-cyclopropane-1-carboxylic acid
12-Ado—12-amino dodecanoic acid
Aic—2-aminoindane-2-carboxylic acid
6-Ahx—6-amino hexanoic acid
8-Aoc—8-amino octanoic acid
aminoheptanoyl—$NH_2$—$(CH_2)_6CO$—
Arg(Mtr)—$N^G$-4-methoxy-2,3,6-trimethylbenzenesulfonyl-arginine
Arg(Me)—$N^G$-methyl-arginine
Arg($NO_2$)—$N^G$-nitro-arginine
Arg(Pbfo—$N^G$-pentamethyldihydrobenzofuransulfono-arginine
Arg(Pmc)—$N^G$-pentamethylchromansulfonyl-arginine
Arg(Tos)—$N^G$-tosyl-arginine
Asp(anilino)—beta-anilino-aspartic acid
Asp(3-Cl-anilino)—beta-(3-chloro-anilino)-aspartic acid
Asp(3,5-diCl-anilino)—beta-(3,5-dichloro anilino)-aspartic acid
D/L Atc—(D,L)-2-aminotetralin-2-carboxylic acid
11-Aun—11-amino undecanoic acid
AVA—5-amino valeric acid
Bip—biphenylalanine
Bz—benzoyl
Cha—cyclohexylalanine
Chg—cyclohexylglycine
Dip—3,3-ciphenylalanine
Et—ethyl
GBZA—4-guanidino benzoic acid
B-Gpa—3-guanidino propionic acid
Hphe—homophenylalanine
Lys(Z)—N-epsilon-benzyloxycarbonyl-lysine
Me—methyl
Nal 1—3-(1-naphthyl)alanine
Nal 2—3-(2-naphthyl)alanine Phg—phenylglycine
pF-Phe—para-fluoro-phenylalanine
Phe(4-Br)—4-bromo-phenylalanine
Phe(4-CF$_3$)—4-trifluoromethyl-phenylalanine
Phe(4-Cl)—4-chloro-phenylalanine
Phe(2-Cl)—2-chloro-phenylalanine
Phe(2,4-diCl)—2,4,-dichloro-phenylalanine
Phe(3,4-diCl)—3,4,-dichloro-phenylalanine
Phe(3,4-diF)—3,4,-difluoro-phenylalanine
Phe(4-I)—4-iodo-phenylalanine
Phe(3,4-di-OMe)—3,4,-dimethoxy-phenylalanine
Phe(4-Me)—4-methyl-phenylaianine
Phe(4-NO$_2$)—4-nitro-phenylalanine
Qal(2')—beta-(2-quinolyl)-alanine
Sal—3-styrylalanine
Ser(Bzl)—O-benzyl-serine
TFA—trifluoroacetyl
Tic—1,2,3,4-tetrahydroisoquinoline-3-carboxylic acid
Tle—tert-butylalanine In the listing of peptides according to the present invention, conventional amino acid residues have their conventional meaning as given in Chapter 2400 of the *Manual of Patent Examining Procedure*, 8$^{th}$ Ed. Thus "D-Phe" is D-phenylalanine; "Arg" is arginine; "Trp" is tryptophan and so on.

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue".

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl groups of the designated length in either a straight or branched configuration. Examples of such alkyl groups include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical—$R^aR^b$ where $R^a$ is an alkylene group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group CH$_3$CO—.

A peptide or aliphatic moiety is "acylated" when an alkyl or substituted alkyl group as defined above is bonded through one or more carbonyl {—(C=O)—} groups. A peptide is most usually acylated at the N-terminus.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatc rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—CO.NH$_2$), such as for example methylamide, ethylamide, propylamide, and the like.

An "imide" includes compounds containing an imido group (—CO.NH.CO—).

An "amine" includes compounds that contain an amino group (—NH$_2$).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

The term "halogen" is intended to include the halogen atoms fluorine, chlorine, bromine and iodine, and groups including one or more halogen atoms, such as —CF$_3$ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound or peptide of the present invention and a pharmaceutically acceptable carrier.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by a melanocortin receptor agonist agent.

By "binding affinity" is meant the ability of a compound or drug to bind to its biological target.

Peptides of the Invention

Peptides of Formula I. The peptides encompassed in formula I are exemplified by the following disclosed peptides. In the peptide $NH_2-(CH_2)_6CO-Ser(Bzl)-D-Phe(4-Cl)-Arg$, as further disclosed in Example 1, $R_1$ is an omega amino derivatve of a $C_5$ aliphatic linear chain consisting of $NH_2-(CH_2)_5$, $R_2$ is H, $R_3$ is an amino acid side chain moiety of Ser(Bzl):

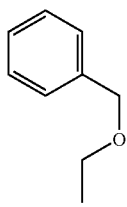

$R_4$ is an amino acid side chain moiety of D-Phe(4-Cl):

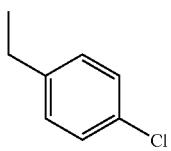

$R_5$ is an amino acid side chain moiety of Arg:

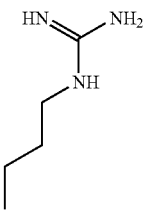

and $R_6$ is —OH. It is to be understood that here and elsewhere in the specification and claims an amino acid sequence wherein there is not specified a C-terminus group, such as the foregoing, the peptide is a free acid compound with an C-terminus —OH, such that $NH_2-(CH_2)_6CO-Ser(Bzl)-D-Phe(4-Cl)-Arg-OH$ is an alternative and identical description of the peptide $NH_2-(CH_2)_6CO-Ser(Bzl)-D-Phe(4-Cl)-Arg$.

In another example, in the peptide $NH_2-(CH_2)_6-CO-Ser(Bzl)-D-Phe(4-Cl)-Arg-NH_2$, as further disclosed in Example 2, $R_1$, $R_2$, $R_3$, $R_4$, and $R_5$ are as above, and $R_6$ is —$NH_2$.

In another example, in the peptide $NH_2-(CH_2)_6-CO-Ser(Bzl)-D-Nal\ 2-Arg$, as further disclosed in Example 3, $R_1$, $R_2$, $R_3$, and $R_5$ are as above, $R_4$ is an amino acid side chain moiety of D-Nal 2:

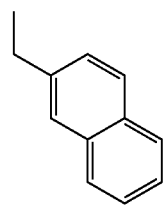

and $R_6$ is —OH.

In another example, in the peptide $NH_2-(CH_2)_6-CO-Ser(Bzl)-D-Nal\ 2-Arg-NH_2$, as further disclosed in Example 4, $R_1$, $R_2$, $R_3$, $R_4$, and $R_5$ are as above, and $R_6$ is —$NH_2$.

In another example, in the peptide $NH_2-(CH_2)_6-CO-Ser(Bzl)-D-Phe(4-Cl)-Arg(NO_2)$, as further disclosed in Example 5, $R_1$, $R_2$, $R_3$, and $R_4$ are as above, $R_5$ is an amino acid side chain moiety of Arg($NO_2$):

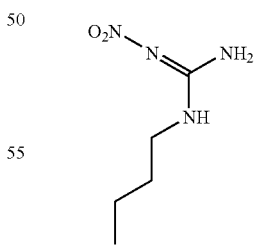

and $R_6$ is —OH.

In another example, in the peptide $NH_2-(CH_2)_6-CO-Ser(Bzl)-D-Phe(4-Cl)-Cit$, as further disclosed in Example 6, $R_1$, $R_2$, $R_3$, and $R_4$ are as above, $R_5$ is an amino acid side chain moiety of Cit:

and $R_6$ is —OH.

In another example, in the peptide NH$_2$—(CH$_2$)$_6$—CO-Ser(Bzl)-D-Phe(4-Cl)-Lys, as further disclosed in Example 7, R$_1$, R$_2$, R$_3$, and R$_4$ are as above, R$_5$ is an amino acid side chain moiety of Lys:

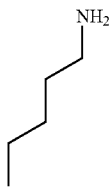

and R$_6$ is —OH.

In another example, in the peptide NH$_2$—(CH$_2$)$_6$—CO-Ser(Bzl)-D-Phe(4-Cl)-Orn, as further disclosed in Example 8, R$_1$, R$_2$, R$_3$, and R$_4$ are as above, R$_5$ is an amino acid side chain moiety of Orn:

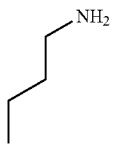

and R$_6$ is —OH.

In another example, in the peptide NH$_2$—(CH$_2$)$_6$—CO-Ser(Bzl)-D-Phe(4-Cl)-Ala, as further disclosed in Example 9, R$_1$, R$_2$, R$_3$, and R$_4$ are as above, R$_5$ is an amino acid side chain moiety of Ala:

and R$_6$ is —OH.

In another example, in the peptide NH$_2$—(CH$_2$)$_6$—CO-Ser(Bzl)-D-Ala-Arg, as further disclosed in Example 10, R$_1$, R$_2$, and R$_3$ are as above, R$_4$ is an amino acid side chain moiety of D-Ala:

R$_5$ is an amino acid side chain moiety of Arg as above and R$_6$ is —OH.

In another example, in the peptide NH$_2$—(CH$_2$)$_6$—CO-Ala-D-Phe(4-Cl)-Arg, as further disclosed in Example 11, R$_1$, R$_3$, R$_4$, and R$_5$ are as above, R$_2$ is an amino acid side chain moiety of Ala as above and R$_6$ is —OH.

In another example, in the peptide Ser(Bzl)-D-Phe(4-Cl)-Arg, as further disclosed in Example 12, m is 0, such that a single H occupies the position specified by m, R$_3$, R$_4$, and R$_5$ are as above, and R$_6$ is —OH.

In yet another example, in the peptide Ac-Ser(Bzl)-D-Phe(4-Cl)-Arg, as further disclosed in Example 13, R$_1$ and R$_2$ are each H, R$_3$, R$_4$, and R$_5$ are as above, and R$_6$ is —OH.

Pharmaceutical Compositions of the Invention. The pharmaceutical compositions of the invention may further be defined as a composition for treating sexual dysfunction in a mammal which includes a peptide or a pharmaceutically acceptable salt thereof of the formula:

$$Y\text{-}Xaa_1\text{-}Xaa_2\text{-}Z \qquad \qquad III$$

wherein Y is H, an acyl group with a linear or branched C$_1$ to C$_{17}$ alkyl, aryl, heteroaryl, alkene, alkenyl or aralkyl chain including an NH$_2$, NH$_3^+$, or NH group or a corresponding acylated derivative, or is an amino add, a dipeptide or a tripeptide, with the side chains thereof independently selected from H or a linear or branched C$_1$ to C$_{17}$ alkyl, aryl, heteroaryl, alkene, alkenyl or aralkyl chain, with an N-terminus NH$_2$, NH$_3^+$, NH group or a corresponding acylated derivative; Xaa$_1$ and Xaa$_2$ are independently each an L- or D-amino acid with a side chain containing a C$_1$ to C$_6$ aliphatic linear or branched chain or an L- or D-amino acid with a side chain containing at least one aromatic moiety, on the proviso that at least one of Xaa$_1$ and Xaa$_2$ is an L- or D-amino acid with a side chain containing at least one aromatic moiety; Z is —OH, NH$_2$, NH—R, a C$_1$ to C$_6$ aliphatic amino acid side chain moiety, or is an amino add with a side chain selected from H, a C$_1$ to C$_6$ aliphatic amino acid side chain moiety or a neutral hydrogen bonding or positively charged amino acid side chain moiety, with a C-terminus —OH, NH$_2$, or NH—R; and R is an aliphatic C$_1$ to C$_{17}$ chain.

It may thus be seen that the minimum construct of formula III is a dipeptide, and that the maximum construct is a hexapeptide. The construct of formula III may further include structures defined herein as an amino acid residue, such as for example Y can be aminoheptanoyl.

In one preferred embodiment, Xaa$_1$ and Xaa$_2$ are each independently an L- or D-amino acid with a side chain containing at least one aromatic moiety.

It is to be understood that here and elsewhere reference to "C-terminus amino acid(s)" refers to the amino acid residue(s) occupying the C-terminus position in the peptide, which is to say the position conventionally occupied in a peptide with a terminal amino acid with a free carboxyl group, it being understood that the terminal group of the C-terminus amino acid need not be a carboxyl group, and may be, as specified herein, another group, including —NH$_2$ (amide) or —NH—R (substituted amide), where R is for example an aliphatic C$_1$ to C$_{17}$ chain.

It may thus be seen that in one embodiment, such as wherein Z is not an amino acid residue, the invention is characterized, in part, as a peptide of from two to about five amino acid residues, wherein the C-terminus amino acid residues are Phe-Arg or mimetics or homologs thereof, including without limitation all known derivatives and isomers of Phe and of Arg, and further optionally wherein the C-terminus group is —OH or —NH$_2$. In a preferred embodiment, the C-terminus amino acid residues are D-Phe-Arg or mimetics or homologs thereof, including without limitation known derivatives of D-Phe and of Arg. Derivatives of Phe include, by way of example and not limitation, L- or D-isomers of Phe, pF-Phe, Phe(4-Br), Phe(4-CF$_3$), Phe(4-Cl), Phe(2-Cl), Phe(2,4-diCl), Phe(3,4-diCl), Phe(3,4-diF), Phe(4-I), Phe(3,4-diOMe), Phe(4-Me), or Phe(4-NO$_2$), among other variants of Phe. Derivatives of Arg include, by way of example and not limitation, L- or D-isomers of Arg, Arg(NO$_2$), Arg(Tos), Arg(Pbf)), Arg(Mtr), Arg(Me), and Arg(Pmc), among other variants of Arg.

The pharmaceutical composition may further be characterized in that the peptide does not inhibit the binding of α-MSH or an α-MSH analog to melanocortin receptors. Thus the peptide does not inhibit the binding of α-MSH or an α-MSH analog to MC4-R. Similarly, the peptide does not inhibit the binding of α-MSH or an α-MSH analog to MC3-R. In a preferred embodiment, the peptide is not a melanocortin receptor agonist, and specifically is not a MC4-R receptor agonist or a MC3-R agonist.

The invention further includes other compounds and structures that are functionally equivalent to the peptides of this invention. These other compounds are characterized in part as effective in inducting erectile activity, preferably at very low doses, without being specific for any known melanocortin receptor, while having structural similarities to a His-Phe, Phe-Arg or His-Phe-Arg construct. These other compounds may further be characterized as specific for the class of receptors, which may be protein receptors or enzyme-associated receptors, for which the peptides of this invention are specific.

In one preferred embodiment, $Xaa_1$ is Ser(Bzl). In another preferred embodiment, $Xaa_1$ includes Phe or Nal. Here and elsewhere, an amino acid residue specific formula reference, such as for example $Xaa_1$, is said to "include" or "comprise" an amino acid, such as for example Phe, when such amino acid residue is Phe or a derivative or isomer thereof, including a derivative of an amino acid side chain moiety as defined herein. Thus, for example, Phe includes L- or D-isomers of Phe, pF-Phe, Phe(4-Br), Phe(4-$CF_3$), Phe(4-Cl), Phe(2-Cl), Phe(2,4-diCl), Phe(3,4-diCl), Phe(3,4-diF), Phe(4-I), Phe(3,4-di-OMe), Phe(4-Me), and Phe(4-$NO_2$). Nal includes L- or D-isomers of Nal, Nal 1 or Nal 2. In another preferred embodiment, $Xaa_2$ includes Phe or Nal, both as described above.

In yet another embodiment, either $Xaa_1$ or $Xaa_2$ may be L- or D-Ala.

In general, $Xaa_1$ or $Xaa_2$, and in a preferred embodiment both, can include any amino acid residue including at least one aromatic moiety, which at least one aromatic moiety can optionally be functionalized with at least one halogen, alkyl group or aryl group. Thus the amino acid residue in the $Xaa_1$ or the $Xaa_2$ position, or both, may have, for example, a side chain such as any of the following:

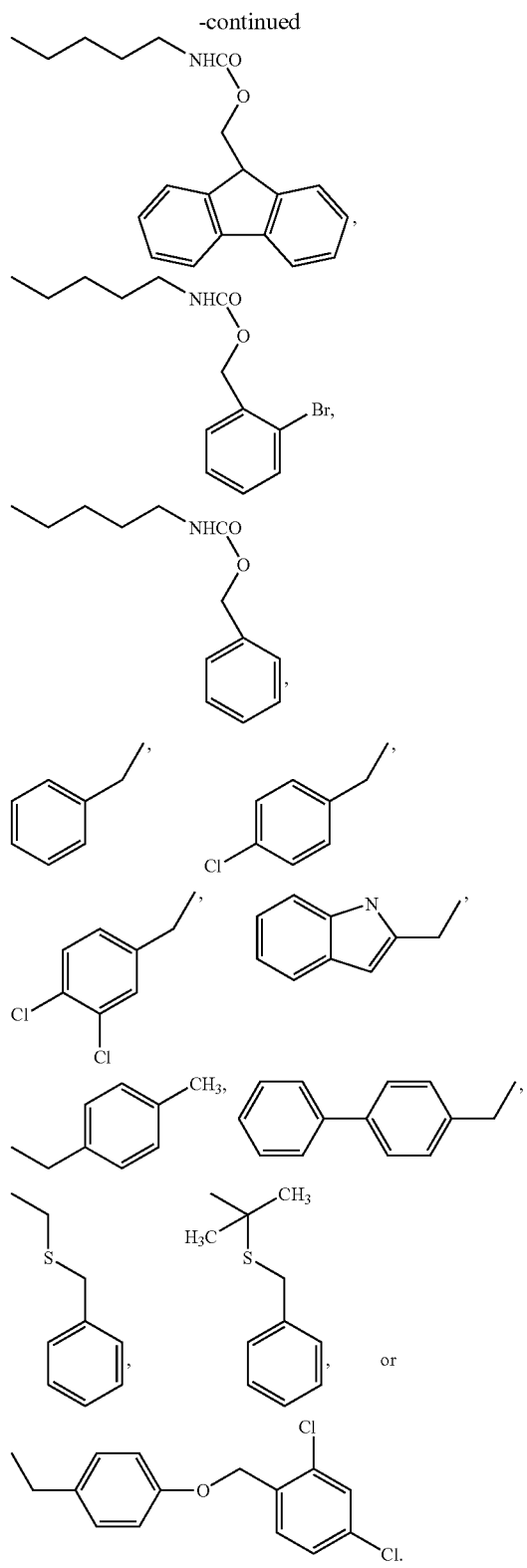

In an alternative embodiment, $Xaa_1$ or the $Xaa_2$ position, or both, may be a derivatized, modified, synthetic or unnatural amino acid, such as by way of example only any of the following, which may further include isomers of the following:

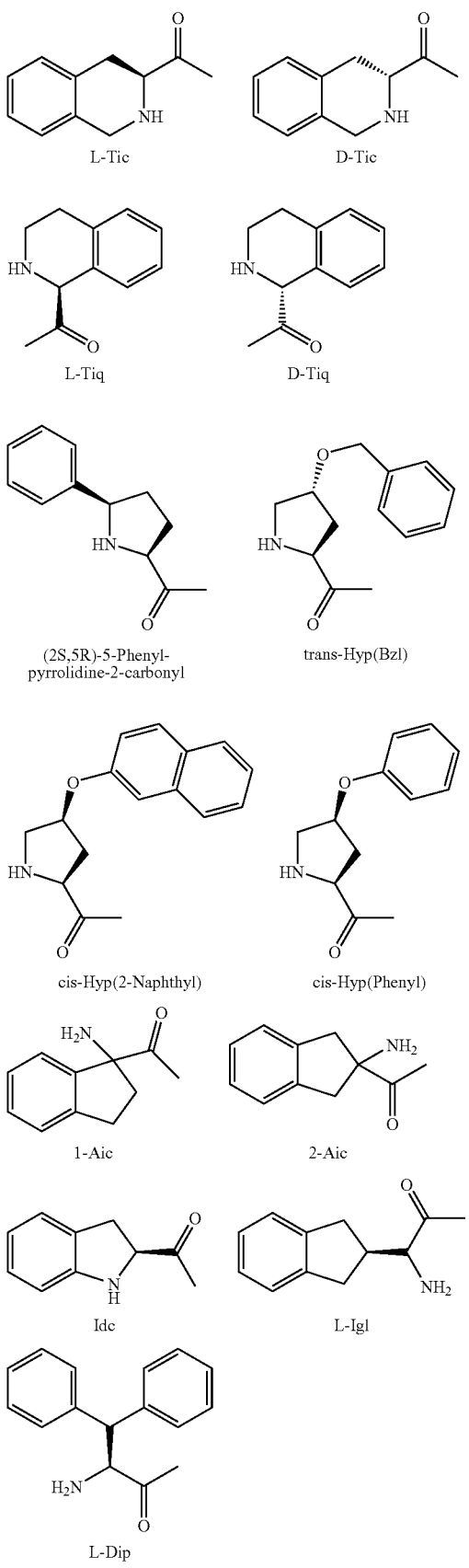

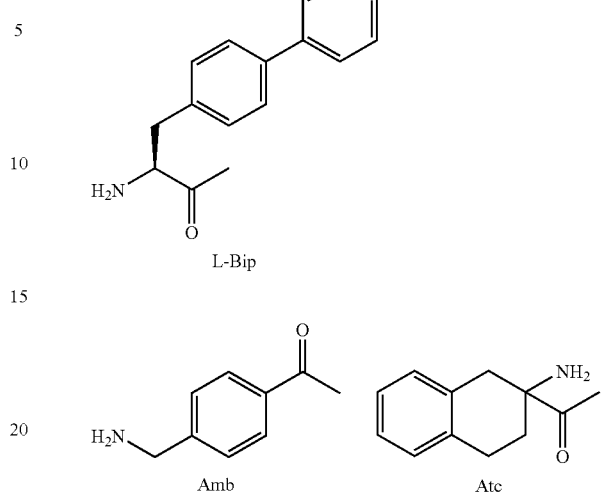

In a preferred embodiment, Y is aminoheptanoyl. Y may also include an acyl group, such as an acetyl group.

In a preferred embodiment, Z includes Arg. Thus Arg may be an L- or D-isomer of Arg, Arg(NO$_2$), Arg(Tos), Arg(Pbf)), Arg(Mtr), Arg(Me), or Arg(Pmc). Alternatively Z may include Cit, Lys or Orn. Z may also include an L- or D-amino acid with a side chain containing a neutral hydrogen bonding or positively charged moiety. Thus any of the amino acids containing at least one aromatic side chain moiety specified for Xaa$_1$ or Xaa$_2$ may be Z, provided that such amino acid side chain contains a neutral hydrogen bonding or positively charged moiety. Optionally the neutral hydrogen bonding or positively charged amino acid side chain moiety is an amino acid side chain moiety derived from a natural or synthetic L- or D-amino acid, wherein the moiety includes at least one nitrogen-containing group, including an amide, imide, amine, urea, urethane, guanidine or nitrile. In one preferred embodiment, the nitrogen-containing amino acid side chain moiety is selected from the following:

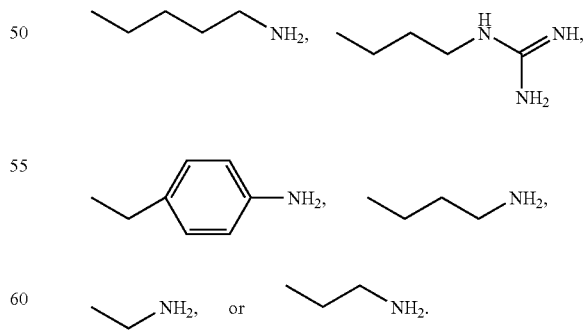

The neutral aliphatic amino acid side chain moiety, which side chain includes hydrogen donors and/or acceptors, can be selected from the following:

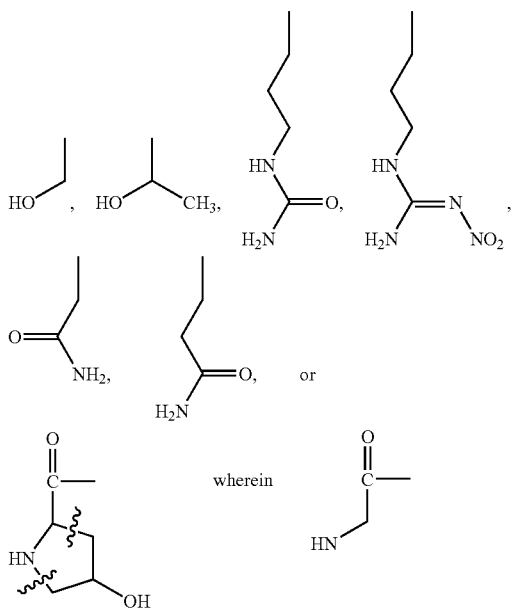

is a portion of the backbone, and the amino acid side chain moiety is

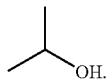

In a preferred embodiment of the pharmaceutical composition, the peptide comprises no more than five amino acids. In a more preferred embodiment, the peptide comprises four amino acids. In yet another preferred embodiment, the peptide comprises three amino acids. In the peptide, there can be provided an N-terminus aliphatic $C_1$ to $C_{17}$ moiety, which may be linear or branched, and may be an alkyl, aryl, heteroaryl, alkene, alkenyl or aralkyl chain. The N-terminus aliphatic $C_1$ to $C_{17}$ moiety may be an acetylated derivative, such as an acetylated derivative of an omega amino acid derivative of an aliphatic $C_1$ to $C_{17}$ moiety. In one preferred embodiment, the N-terminus moiety is $NH_2$—$(CH_2)_6$—CO—.

In yet another embodiment, the invention provides a compound and method of treating sexual dysfunction in a mammal, comprising administration of a therapeutically effective amount of a peptide of formula IV:

aminoheptanoyl-$Xaa_4$-$Xaa_5$-$Xaa_6$                IV or a pharmaceutically acceptable salt thereof, wherein $Xaa_4$ and $Xaa_5$ are independently each an L- or D-amino acid with a side chain containing at least one aromatic moiety; $Xaa_6$ comprises an amino acid with a side chain selected from H, a $C_1$ to $C_6$ aliphatic amino acid side chain moiety or a neutral hydrogen bonding or positively charged amino acid side chain moiety, with a C-terminus —OH, $NH_2$, or NH—R; and R is a $C_1$ to $C_{17}$ chain.

In the method and compounds of formula IV, $Xaa_4$ may be Ser(Bzl). $Xaa_5$ may be Phe, including an L- or D-isomer of Phe, pF-Phe, Phe(4-Br), Phe(4-$CF_3$), Phe(4-Cl), Phe(2-Cl), Phe(2,4-diCl), Phe(3,4-diCl), Phe(3,4-diF), Phe(4-I), Phe(3, 4-di-OMe), Phe(4-Me), or Phe(4-$NO_2$). Alternatively, $Xaa_5$ may be Nal, including an L- or D-isomer of Nal, Nal 1 or Nal 2. $Xaa_6$ may be Arg, including an L- or D-isomer of Arg, Arg($NO_2$), Arg(Tos), Arg(Pbf), Arg(Mtr), Arg(Me), or Arg (Pmc).

The method of use of a compound of formula IV may further include administration of a therapeutically effective amount of a second sexual dysfunction pharmaceutical agent. The second sexual dysfunction pharmaceutical agent may be an MC4-R agonist, such as Ac-Nle-cyclo(Asp-His-D-Phe-Arg-Trp-Lys)-OH. Alternatively, the second sexual dysfunction pharmaceutical agent may be a PDE-5 inhibitor, such as sildenafil. The second sexual dysfunction pharmaceutical agent may also be testosterone or an estrogen agonist/antagonist.

In any of the foregoing embodiments, including those of formulas I through IV, the peptide may optionally be further modified so as to be a cyclic peptide. A cyclic peptide can be obtained by inducing the formation of a covalent bond between an amino group at the N-terminus of the peptide, if provided, and a carboxyl group at the C-terminus, if provided. A cyclic peptide can also be obtained by forming a covalent bond between a terminal reactive group and a reactive amino acid side chain moiety, or between two reactive amino acid side chain moieties. One skilled in the art would know that the means by which a given peptide is made cyclic is determined by the reactive groups present in the peptide and the desired characteristic of the peptide.

Peptide Synthesis. The peptides of this invention may be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group or other reactive groups protected and the free primary carboxyl group of another amino acid or residue thereof having its amino group or other reactive groups protected. In a preferred conventional procedure, the peptides of this invention may be synthesized by solid-phase synthesis and purified according to methods known in the art. Any of a number of well-known procedures utilizing a variety of resins and reagents may be used to prepare the peptides of this invention.

The process for synthesizing the peptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Solid phase peptide synthesis methods are well known and practiced in the art. In such a method the synthesis of peptides of the invention can be carried out by sequentially incorporating the desired amino acid residues one at a time into the growing peptide chain according to the general principles of solid phase methods. These methods are disclosed in numerous references, including, Merrifield, R. B., Solid phase synthesis (Nobel lecture). *Angew Chem* 24:799-810 (1985) and Barany et al., *The Peptides, Analysis, Synthesis and Biology*, Vol. 2, Gross, E. and Meienhofer, J., Eds. Academic Press 1-284 (1980).

In chemical syntheses of peptides, reactive side chain groups of the various amino acid residues are protected with suitable protecting groups, which prevent a chemical reaction from occurring at that site until the protecting group is removed. Usually also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyt (Moz); aliphatic urethane-type protecting groups, such as t-butyloxycarbonyl (Boc), diisopropylmethoxycarbonyl, isopropoxycarbonyl, and allyloxycarbonyl. Fmoc is preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, and Boc. Pmc is a preferred protecting group for Arg.

The peptides of the invention described herein were prepared using solid phase synthesis, in most cases by means of a Symphony Multiplex Peptide Synthesizer (Rainin Instrument Company) automated peptide synthesizer, using programming modules as provided by the manufacturer and following the protocols set forth in the manufacturer's manual.

Solid phase synthesis was commenced from the C-terminal end of the peptide by coupling a protected alpha amino acid to a suitable resin. Such a starting material can be prepared by attaching an alpha amino-protected amino acid by an ester linkage to a p-benzyloxybenzyl alcohol (Wang) resin or a 2-chlorotrityl chloride resin, by an amide bond between an Fmoc-Linker, such as p-[(R,S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in DMF may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Methods for N-terminus modification, such as acetylation, or C-terminus modification, such as amidation, are well known in the art. Similarly, methods for modifying side chains of amino acids are well known to those skilled in the art of peptide synthesis. The choice of modifications made to reactive groups present on the peptide will be determined, in part, by the characteristics that are desired in the peptide.

Following cleavage of peptides from the solid phase following their synthesis, the peptide can be purified by any number of methods, such as reverse phase high performance liquid chromatography (RP-HPLC), using a suitable column, such as a C-18 column. Other methods of separation or purification, such as methods based on the size or charge of the peptide, can also be employed. Once purified, the peptide can be characterized by any number of methods, such as high performance liquid chromatograph (HPLC), amino acid analysis, mass spectrometry, and the like.

Melanocortin Receptor Binding Assays. The peptides of the invention are characterized, in part, in that they do not inhibit the binding of α-MSH or an α-MSH analog to melanocortin receptors, and specifically MC1-R, MC3-R, MC4-R or MC5-R, such as by means of a competitive inhibition binding assay. Thus the peptide does not inhibit the binding of α-MSH or an α-MSH analog to MC4-R. NDP-MSH is one example of an α-MSH analog. Similarly, the peptide does not inhibit the binding of α-MSH or an α-MSH analog to MC3-R. The peptide is further not a melanocortin receptor agonist, and is specifically not a MC4-R agonist or a MC3-R agonist.

Competitive inhibition binding assay was conducted using membranes prepared from hMC3-R, hMC4-R, hMC5-R, and B-16 mouse melanoma cells (containing MC1-R) using 0.4 nM $^{125}$I-NDP-MSH (0.2 nM for MCL-R) (New England Nuclear, Boston, Mass., USA) in 50 mM HEPES buffer containing 1 mM $MgCl_2$, 2 mM $CaCl_2$, and 5 mM KCl, at pH 7.2. The assay tube also contained a chosen concentration of the peptides of this invention, for determining inhibition of the binding of $^{125}$I-NDP-MSH to its receptor. Non-specific binding was measured by complete inhibition of binding of $^{125}$I-NDP-MSH in the assay in the presence of 1 μM α-MSH. Incubation was for 90 minutes at 37° C., after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 μM α-MSH. The cpm obtained in the presence of peptides of this invention were normalized with respect to 100% specific binding to determine the percent inhibition of $^{125}$I-NDP-MSH binding. Each assay was conducted in triplicate.

A peptide did not "inhibit" α-MSH binding, determined by inhibition of binding of $^{125}$I-NDP-MSH, when the measured percent inhibition was less than 10%, and preferably when no inhibition was detectable (the measured percent inhibition was 0% or less).

Functional assays to determine agonist or antagonist status of a test peptide may be conducted by any means known in the art. In one method, a cAMP assay is performed. Human MC4-R cells are grown to confluence in 96 well plates (plating approximately 250,000 cells per well). Identical sets of cells in triplicate are treated with 0.2 mM isobutylmethylxanthine (IBMX) and the chosen concentration of the peptide or alternatively the peptide in the presence of 20 nM NDP-MSH. Cells similarly treated but with only 20 nM NDP-MSH serve as positive control in a volume of 200 μL. A buffer blank, as a negative control, is also included. Incubation is for one hour at 37° C. after which the cells are lysed by the addition of 50 μL of a cell lysis buffer. Total cAMP accumulated in 250 μL of this solution is quantitated using a commercially available low pH cAMP assay kit (Amersham BioSciences) by the procedure specified by the kit supplier. Any peptide (not one of this invention) showing cAMP accumulation in the same range as or higher than the positive control (buffer blank in the presence of α-MSH) is considered to be an agonist. A peptide showing accumulation in the same range as the negative control (buffer blank in the absence of α-MSH) is ineffective at the test concentration if the result is similar to the positive control where α-MSH is also present in the assay. A peptide (not one of this invention) showing accumulation in the same range as the negative control is considered to be an antagonist if there is inhibition in CAMP when α-MSH is present in the assay. Similar methods may be employed for MC3-R, using MC3-R cells. Peptides of this invention are ineffective at any concentration, and thus are neither an agonist nor an antagonist with respect to MC4-R.

Formulation and Utility.

The peptides and pharmaceutical compositions of this invention can be used for both medical applications and animal husbandry or veterinary applications. Typically, the peptide or pharmaceutical composition is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Therapeutic Application in Males. The peptides and pharmaceutical compositions of this invention may be used to treat male sexual dysfunction, including erectile dysfunction or impotence.

Therapeutic Application in Females. The peptides and pharmaceutical compositions of this invention may be used to treat female sexual dysfunction, including without limitation sexual arousal disorder.

Diagnostic Application. The peptides of this invention may be used for diagnostic purposes, to diagnose causes of erectile dysfunction in males, or sexual dysfunction in mammals generally. Thus, the peptides may be administered and the erectile reaction of the patient monitored.

Salt Form of Peptides. The peptides of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the peptides of this invention are prepared in a suitable solvent from the peptide and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the peptides of this invention include an acidic moiety, suitable pharmaceutically acceptable salts may include alkali metal salts, such as sodium or potassium salts, or alkaline earth metal salts, such as calcium or magnesium salts.

Pharmaceutical Compositions. The invention provides a pharmaceutical composition that includes a peptide of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The peptide compositions of this invention may be formulated or compounded into pharmaceutical compositions that include at least one peptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of this invention over a period of time.

In practical use, the peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or non-aqueous techniques. The amount of active peptide in such therapeutically useful compositions is such that an effective dosage will be obtained. In another advantageous dosage unit form, sublingual constructs may be employed, such as sheets, wafers, tablets or the like. The active peptides can also be administered intranasally as, for example, by liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Peptides may also be administered parenterally. Solutions or suspensions of these active peptides can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Peptides may also be administered by transurethral delivery. The formulation for transurethral delivery may contain one or more selected carriers or excipients, such as water, silicone, waxes, petroleum jelly, polyethylene glycol, propylene glycol, liposomes, sugars such as mannitol and lactose, and/or a variety of other materials, with polyethylene glycol and derivatives thereof particularly preferred. Depending on the peptide administered, it may be desirable to incorporate a transurethral permeation enhancer in the urethral dosage form. Examples of suitable transurethral permeation enhancers include dimethylsulfoxide, dimethyl formamide, N,N-dimethylacetamide, decylmethylsulfoxide ($C_{10}MSO$), polyethylene glycol monolaurate, glycerol monolaurate, lecithin, alcohols, such as ethanol, detergents, and the like. Transurethral formulations may additionally include one or more enzyme inhibitors effective to inhibit peptide degrading enzymes which may be present in the urethra. Such enzyme inhibiting compounds may be determined by those skilled in the art by reference to the pertinent literature and/or using routine experimental methods. Additional optional components include excipients, preservatives, such as antioxidants, chelating agents, solubilizing agents, such as surfactants, and the like, as will be appreciated by those skilled in the art of drug formulation preparation and delivery.

Transurethral drug administration can be carried out in a variety of different ways using a variety of urethral dosage forms. For example, the peptide in an appropriate formulation can be introduced into the urethra through a flexible tube, squeeze bottle, pump, or aerosol spray. The peptide may also be contained in coatings, pellets, or suppositories which are absorbed, melted, or bioeroded in the urethra. In certain embodiments, the peptide is included in a coating on the exterior surface of a penile insert.

Peptides of this invention may also be administered vaginally. The delivery system can be a solid object such as a tampon, tampon-like device, vaginal ring, cup, pessary, tablet, or suppository. Alternatively it can be a composition in the form of a cream, paste, ointment, or gel having a sufficient thickness to maintain prolonged contact with vaginal epithelium. Alternatively, it can be a coating on a suppository wall or a sponge or other absorbent material impregnated with a liquid drug formulation further containing a solution, lotion, or suspension of bioadhesive particles, for example. Any form of drug delivery system which will effectively deliver the peptide to the vaginal endothelium is intended to be included within the scope of this invention.

The peptides of this invention may be therapeutically applied by means of nasal administration. By "nasal administration" is meant any form of intranasal administration of any of the peptides of this invention. The peptides may be in an aqueous solution, such as a solution including saline, citrate or other common excipients or preservatives. The peptides may also be in a dry or powder formulation.

In an alternative embodiment, peptides of this invention may be administered directly into the lung. Intrapulmonary administration may be performed by means of a metered dose inhaler, a device allowing self-administration of a metered bolus of a peptide of this invention when actuated by a patient during inspiration.

The peptides of this invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the peptide may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the peptide may be in a dried and particulate form. In a preferred embodiment, the particles are between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 µm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

In one preferred embodiment, a dry powder inhaler is employed which includes a piezoelectric crystal that deaggregates a dry powder dose, creating a small powder "cloud." Once the powder cloud is generated, an electrostatically charged plate above the powder cloud lifts the drug into the air stream. The user with one relatively easy breath can then inhale the powder. The device may be breath activated, utilizing a flow sensor that activates the electronic components upon the start of inhalation, and thereby eliminating the need for coordination of activation and breathing rhythms by the user.

Routes of Administration. If it is administered by injection, the injection may be intravenous, subcutaneous, intramuscular, intraperitoneal or other means known in the art. The peptides of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

Therapeutically Effective Amount. In general, the actual quantity of peptide of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a peptide or pharmaceutical composition of this invention that is sufficient to therapeutically alleviate sexual dysfunction in a patient, or to prevent or delay onset or recurrence of the sexual dysfunction.

The peptide of the formula $NH_2$—$(CH_2)_6$CO-Ser(Bzl)-D-Phe(4-Cl)-Arg induces a penile erection response in male rats at oral doses of less than 1 μg/kg, and may be biologically active at oral doses as low as 250 ng/kg. Extrapolating to a human, a human dose of $NH_2(CH_2)_6$CO-Ser(Bzl)-D-Phe(4-Cl)-Arg for oral delivery could be as low as 1 mg, and possibly lower.

The peptide of the formula $NH_2$—$(CH_2)_6$Co-Ser(Bzl)-D-Phe(4-Cl)-Arg($NO_2$) had, in rats, an optimal dose response when administered by intranasal means at a dose of about 0.1 μg/kg. Extrapolating to a human, an intranasal dose could be as low as about 1 to about 10 μg.

In general, the peptides of this invention are highly active, with dose responses as low as 0.001 μg/kg, and optimal or peak dose responses between about 0.1 μg/kg and 10 μg/kg, depending on the specific peptide and the route of administration. For example, the peptide can be administered at 0.001, 0.005, 0.01, 0.05, 0.1, 0.5, 1, 5, 10, 50, 100, or 500 μg/kg body weight, depending on specific peptide selected, the desired therapeutic response, the route of administration, the formulation and other factors known to those of skill in the art.

As shown in FIG. 1, the peptides of this invention typically show a "bell-shaped" dose response. That is, at increasing doses the desired biological or physiological response increases, reaches a peak or optimal response, and may thereafter decrease with further increasing doses. Conventional dose response studies and other pharmacological means may be employed to determine the optimal dose for a desired effect, such as inducing penile erections, with a given peptide, given formulation and given route of administration.

Combination Therapy.

It is also possible and contemplated to use the peptides of this invention in combination with other drugs or agents. These other drugs and agents may include melanocortin receptor-specific agents that induce erectile activity, including specifically MC3-R and MC4-R agonists, phosphodiesterase-5 inhibitors, testosterone, prostaglandin and the like. In a preferred embodiment of the invention, peptides of the invention are used in combination with a therapeutically effective amount of a cyclic-GMP-specific phosphodiesterase inhibitor or an alpha-adrenergic receptor antagonist. Similarly, the peptides of this invention may be used in combination with any known mechanical aids or devices.

The present invention thus provides methods of treating sexual dysfunction, the methods comprising the step of administering to the patient having or at risk of having sexual dysfunction a therapeutically effective amount of a peptide of this invention in combination with a therapeutically effective amount of a second sexual dysfunction pharmaceutical agent. The peptide of this invention may be administered simultaneously with, prior to or subsequent to administration with a therapeutically effective amount of a second sexual dysfunction pharmaceutical agent. Preferably the peptide of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the peptide of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the peptide of this invention when desired or needed by the patient.

The present invention thus provides methods of treating sexual dysfunction, the methods comprising the step of administering to a patient having or at risk of having sexual dysfunction a therapeutically effective amount of a peptide of this invention in combination with a compound that is a melanocortin receptor agonist.

The present invention further also provides methods of treating sexual dysfunction, the methods comprising the step of administering to a patient having or at risk of having sexual dysfunction a therapeutically effective amount of a peptide of this invention in combination with a compound that is a melanocortin receptor agonist and in combination with another compound that is useful in the treatment of sexual dysfunction.

In a preferred embodiment of combination therapy the sexual dysfunction is female sexual dysfunction.

In an especially preferred embodiment of combination therapy the sexual dysfunction is erectile dysfunction.

In a preferred embodiment of the foregoing methods, the melanocortin receptor agonist is an agonist of MC3-R or MC4-R, and preferably MC4-R. The agonist may be a nonselective MC3-R and MC4-R agonist.

The present invention also provides pharmaceutical compositions that comprise 1) a peptide of this invention and 2) a compound that is a melanocortin receptor agonist.

The present invention also provides pharmaceutical compositions that comprise 1) a peptide of this invention; 2) a compound that is a melanocortin receptor agonist; and 3) a third compound useful for the treatment of sexual dysfunction.

The present invention also provides pharmaceutical compositions that comprise 1) a peptide of this invention and 2) a second compound useful for the treatment of sexual dysfunction.

Representative agonists of the melanocortin receptor are disclosed in the following publications, which are incorporated here by reference in their entirety: M. E. Hadley et al., Discovery and development of the novel melanogenic drugs, in *Integration of Pharmaceutical Discovery and Development: Case Studies*, edited by Borschart et al., Plenum Press, New York (1998); R. T. Dorr et al., Evaluation of Melanotan-II, A Superpotent Cyclic Melanotropic Peptide in a Pilot Phase-I Clinical Study. *Life Sci* 58:1777-1784 (1996); and R. A. H. Adan, Identification of Antagonists for Melanocortin MC3, MC4, and MC5 Receptors. *Eur J Pharmacol*, 269:331-337 (1994).

In one embodiment of the composition above, the agonists are melanocyte-stimulating hormones (MSH) including α-, β-, and γ-MSH and/or adrenocorticotropic hormones (ACTH).

In another embodiment of the composition above, the melanocortin receptor agonist is Melanotan-II (MT-II). A preferred melanocortin receptor agonist includes any linear or cyclic melanocortin receptor-specific agonist peptide disclosed in International Application WO 03/006620 or a metallopeptide disclosed in International Application WO 02/064091. A particularly preferred melanocortin receptor agonist is Ac-Nle-cyclo(-Asp-His-D-Phe-Arg-Trp-Lys)-OH, as disclosed in U.S. Pat. No. 6,579,968. Alternatively, the agonist may be any agonist disclosed in any of the following patents or patent applications: U.S. Pat. Nos. 6,534,503, 6,472,398, 6,458,790, 6,410,548, 6,376,509, or 6,350,760; U.S. Published Application Nos. 2002/0137664, 2002/0004512, 2002/0143141, or US 2003/0069169; or International Application No. WO 02/18437. The agonist of the melanocortin receptor may preferably be selective for MC4-R.

In an embodiment of the composition above, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphin; oxytocin modulators; α-adrenergic antagonists; androgens; selective androgen receptor modulators (SARMs); buproprion; vasoactive intestinal peptide (VIP); neutral endopeptidase inhibitors (NEP); and neuropeptide Y receptor antagonists (NPY).

In an embodiment of the method and composition, the second sexual dysfunction pharmaceutical agent is testosterone.

In another embodiment of combination therapy, the second sexual dysfunction pharmaceutical agent is a type V phosphodiesterase inhibitor (PDE-5). For example, the PDE-5 inhibitor may be Viagra®, a brand of sildenafil, or may be 1-[[3-(6,7-dihydro-1-methyl-7-oxo-3-propyl-1-H-pyrazolo[4,3-d]pyrimidin-5-yl]-4-ethoxy-phenyl]sufonyl)-4-methylpiperazine citrate salt, as disclosed in U.S. Published Application No. 2003/0083228.

In another embodiment of the composition above, the compound useful for the treatment of sexual dysfunction is an estrogen agonist/antagonist. In one embodiment, the estrogen agonist/antagonist is (−)-cis-6-phenyl-5-[-4-(2-pyrrolidin-1-yl-ethoxy)-phenyl]-5,6,7,8-tetrahydro-napth-thalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a peptide of this invention may be used in combination with any known mechanical aids or devices.

The present invention also provides kits for the treatment of sexual dysfunction (including erectile dysfunction), the kits comprising: a first pharmaceutical composition including a peptide of this invention; a second pharmaceutical composition comprising a second compound useful for the treatment of sexual dysfunction; and, a container for the first and second compositions.

The invention is further illustrated by the following non-limiting examples.

Example 1

Synthesis of $NH_2$—$(CH_2)_6$CO-Ser(Bzl)-D-Phe(4-Cl)-Arg

The peptide $NH_2$—$(CH_2)_6$CO-Ser(Bzl)-D-Phe(4-Cl)-Arg was synthesized by standard solid phase peptide synthesis methods. Briefly, 2-chlorotrityl chloride resin was loaded with Fmoc-Arg(Boc)$_2$-OH. The resin was added to a reaction vessel suitable for solid phase peptide synthesis, and the peptide synthesis was carried out by the sequential steps of Fmoc deprotection, activation and coupling of an Fmoc-amino acid residue, a ninhydrin test, and washing, with the steps repeated for addition of a new amino acid residue at each step. A Boc protected derivative of aminoheptanoyl was used for coupling at the N-terminus. The peptide was cleaved from the resin by treatment with a mixture of 50% TFA—2.5% Triisopropylsilane (TIS) and 2.5% water in dichloromethane (DCM) for 1 hour. The final product was precipitated by adding cold ether and collected by filtration. Final purification was by RP-HPLC using a C-18 column.

The peptide is a linear peptide with a free acid at the C-terminus and an amine group at the N-terminus of the formula:

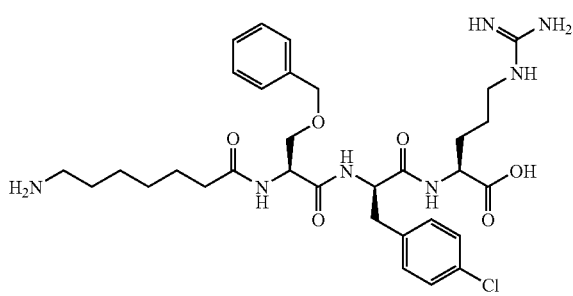

The peptide has a net molecular weight of 660, and was made in a trifluoroacetate salt form.

Example 2

Synthesis of $NH_2$—$(CH_2)_6$—CO-Ser(Bzl)-D-Phe(4-Cl)-Arg-$NH_2$

The peptide $NH_2$—$(CH_2)_6$—CO-Ser(Bzl)-D-Phe(4-Cl)-Arg-$NH_2$ was synthesized by standard solid phase peptide synthesis methods. Briefly, Rink amide resin was added to a reaction vessel suitable for solid phase peptide synthesis, with peptide synthesis carried out by the sequential steps of Fmoc-deprotection, activation, coupling of an Fmoc-amino acid residue, a ninhydrin test, and washing, with the steps repeated for addition of a new amino acid residue at each step. A Boc group was used for protecting the side chain guanidine group of Arg as well as for protecting the amino function of aminoheptanoyl. The peptide was cleaved from resin by treatment with a mixture of 95% TFA—2.5% TIS and 2.5% water for 3 hours. The final product was precipitated by adding cold ether and collected by filtration. Final purification was by RP-HPLC using a C-18 column.

The peptide is a linear peptide with an amide group at the C-terminus and an amine function at the N-terminus of the formula:

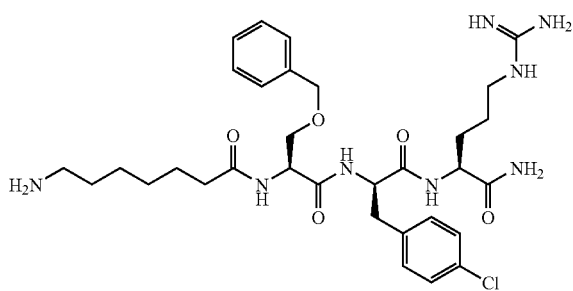

The peptide has a net molecular weight of 659, and was obtained in a trifluoroacetate salt form.

Example 3

Synthesis of $NH_2$—$(CH_2)_6$—CO-Ser(Bzl)-D-Nal 2-Arg

The peptide $NH_2$—$(CH_2)_6$—CO-Ser(Bzl)-D-Nal 2-Arg was synthesized by standard solid phase peptide synthesis methods. Using appropriate Fmoc protected amino acids, the method described in Example 1 was used to synthesize the peptide. Final purification was by RP-HPLC using a C-18 column.

The peptide is a linear peptide with a free acid at the C-terminus and an amine group at the N-terminus of the formula:

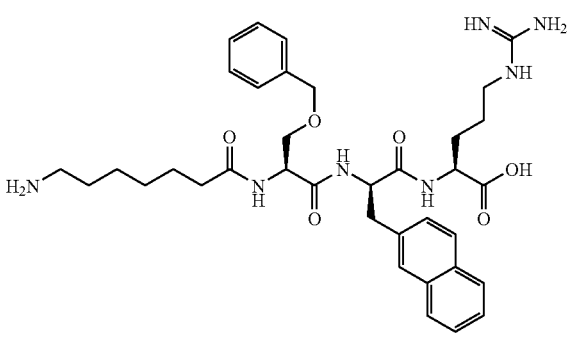

The peptide has a net molecular weight of 675.8, and was obtained in a trifluoroacetate salt form.

Example 4

Synthesis of $NH_2$—$(CH_2)_6$—CO-Ser(Bzl)-D-Nal 2-Arg-$NH_2$

The peptide $NH_2$—$(CH_2)_6$—CO-Ser(Bzl)-D-Nal 2-Arg-$NH_2$ was synthesized by standard solid phase peptide synthesis methods using the general method described in Example 2. Final purification was by RP-HPLC using a C-18 column. The peptide is a linear peptide with an amide group at the C-terminus and an amine group at the N-terminus of the formula:

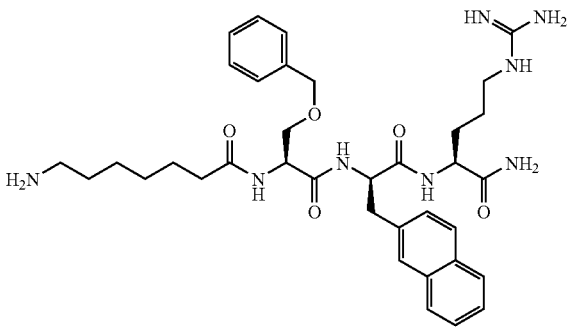

The peptide has a net molecular weight of 674.8, and was isolated as a trifluoroacetate salt.

Example 5

Synthesis of NH₂—(CH₂)₆—CO-Ser(Bzl)-D-Phe(4-Cl)-Arg(NO₂)

The peptide NH₂—(CH₂)₆—CO-Ser(Bzl)-D-Phe(4-Cl)-Arg(NO₂) was synthesized by standard solid phase peptide synthesis methods. Briefly, Fmoc-Arg(NO₂)-Wang resin was added to a solid phase peptide synthesis reaction vessel, with peptide synthesis carried out by the sequential steps of Fmoc-deprotection, activation and coupling of an Fmoc-amino acid residue, a ninhydrin test, and washing, with the steps repeated for addition of a new amino acid residue at each step. A Boc group was used for protecting the amino function of aminoheptanoyl. The peptide was cleaved from the resin using a mixture of 75% TFA—2.5% TIS—2.5% water in DCM for 1 hour. The final product was precipitated by adding cold ether and collected by filtration. Final purification was by RP-HPLC using a C-18 column.

The peptide is a linear peptide with a free acid at the C-terminus and an amine group at the N-terminus of the formula:

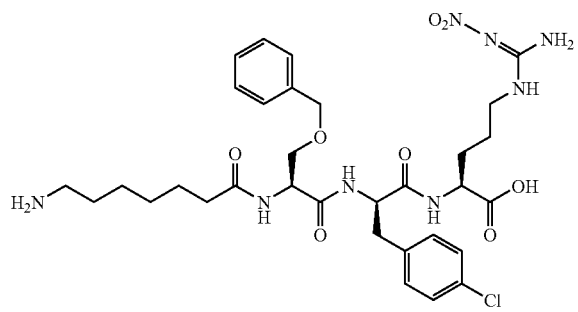

The peptide has a net molecular weight of 705, and was isolated as trifluoroacetate salt.

Example 6

Synthesis of NH₂—(CH₂)₆—CO-Ser(Bzl)-D-Phe(4-Cl)-Cit

The peptide NH₂—(CH₂)₆—CO-Ser(Bzl)-D-Phe(4-Cl)-Cit was synthesized by standard solid phase peptide synthesis methods. Using appropriate Fmoc protected amino acids, the method described in Example 1 was employed. Final purification was by RP-HPLC using a C-18 column.

The peptide is a linear peptide with a free acid at the C-terminus and an amine group at the N-terminus of the formula:

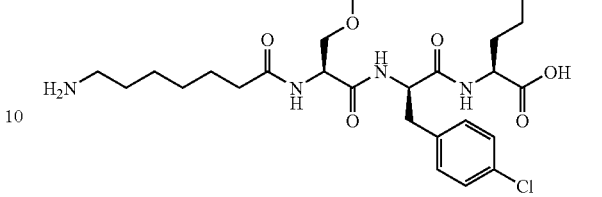

The peptide has a net molecular weight of 661, and was obtained in a trifluoroacetate salt form.

Example 7

Synthesis of NH₂—(CH₂)₆—CO-Ser(Bzl)-D-Phe(4-Cl)-Lys

The peptide NH₂—(CH₂)₆—CO-Ser(Bzl)-D-Phe(4-Cl)-Lys was synthesized by standard solid phase peptide synthesis methods. Using appropriate Fmoc protected amino acids, the method described in Example 5 was employed. Final purification was by RP-HPLC using a C-18 column.

The peptide is a linear peptide with a free acid at the C-terminus and an amine group at the N-terminus of the formula:

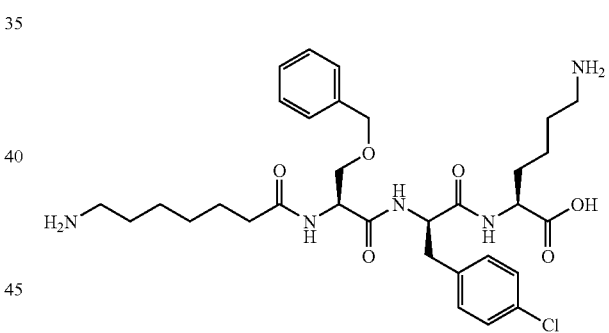

The peptide has a net molecular weight of 632, and was isolated as a trifluoroacetate salt.

Example 8

Synthesis of NH₂—(CH₂)₆—CO-Ser(Bzl)-D-Phe(4-Cl)-Orn

The peptide NH₂—(CH₂)₆—CO-Ser(Bzl)-D-Phe(4-Cl)-Orn was synthesized by standard solid phase peptide synthesis methods. Using appropriate Fmoc protected amino acids, the method described in Example 5 was employed. Final purification was by RP-HPLC using a C-18 column.

The peptide is a linear peptide with a free acid at the C-terminus and an amine group at the N-terminus of the formula:

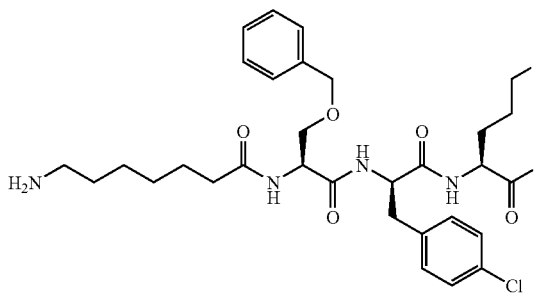

The peptide has a net molecular weight of 618, and was obtained as trifluoroacetate salt form.

Example 9

Synthesis of NH$_2$—(CH$_2$)$_6$—CO-Ser(Bzl)-D-Phe(4-Cl)-Ala

The peptide NH$_2$—(CH$_2$)$_6$—CO-Ser(Bzl)-D-Phe(4-Cl)-Ala was synthesized by standard solid phase peptide synthesis methods. Using appropriate Fmoc protected amino acids, the method described in Example 1 was employed. Final purification was by RP-HPLC using a C-18 column.

The peptide is a linear peptide with a free acid at the C-terminus and an amine group at the N-terminus of the formula:

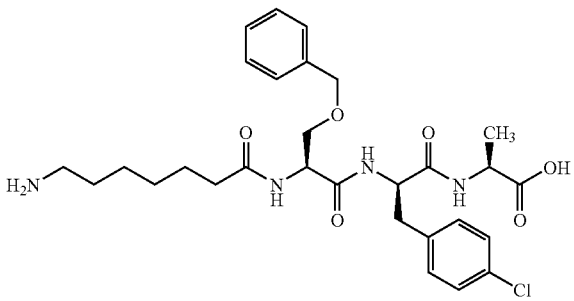

The peptide has a net molecular weight of 575, and was obtained as trifluoroacetate salt.

Example 10

Synthesis of NH$_2$—(CH$_2$)$_6$—CO-Ser(Bzl)-D-Ala-Arg

The peptide NH$_2$—(CH$_2$)$_6$—CO-Ser(Bzl)-D-Ala-Arg was synthesized by standard solid phase peptide synthesis methods. Using appropriate Fmoc protected amino acids, the method described in Example 1 was employed. Final purification was by RP-HPLC using a C-18 column.

The peptide is a linear peptide with a free acid at the C-terminus and an amine group at the N-terminus of the formula:

The peptide has a net molecular weight of 549.7, and was obtained as a trifluoroacetate salt.

Example 11

Synthesis of NH$_2$—(CH$_2$)$_6$—CO-Ala-D-Phe(4-Cl)-Arg

The peptide NH$_2$—(CH$_2$)$_6$—CO-Ala-D-Phe(4-Cl)-Arg was synthesized by standard solid phase peptide synthesis methods. Using appropriate Fmoc protected amino acids, the method described in Example 1 was employed. Final purification was by RP-HPLC using a C-18 column.

The peptide is a linear peptide with a free acid at the C-terminus and an amine group at the N-terminus of the formula:

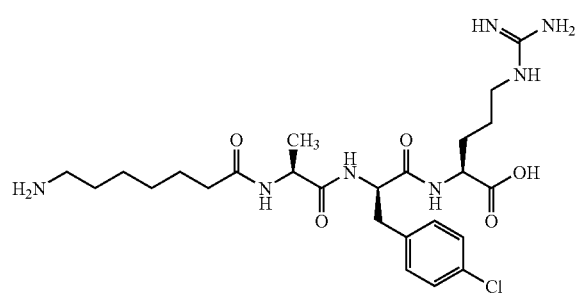

The peptide has a net molecular weight of 554, and was obtained as a trifluoroacetate salt.

Example 12

Synthesis of Ser(Bzl)-D-Phe(4-Cl)-Arg

The peptide Ser(Bzl)-D-Phe(4-Cl)-Arg was synthesized by standard solid phase peptide synthesis methods. Using appropriate Fmoc protected amino acids, the method described in Example 1 was employed. Final purification was by RP-HPLC using a C-18 column.

The peptide is a linear peptide with a free acid at the C-terminus and an amine group at the N-terminus of the formula:

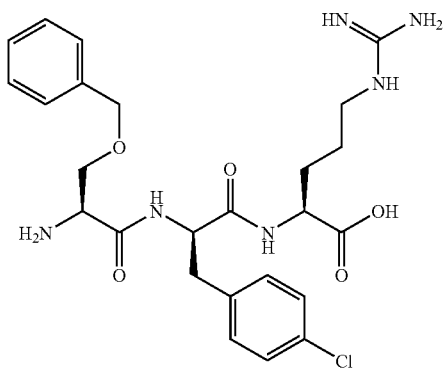

The peptide has a net molecular weight of 533, and was obtained as a trifluoroacetate salt.

Example 13

Synthesis of Ac-Ser(Bzl)-D-Phe(4-Cl)-Arg

The peptide Ac-Ser(Bzl)-D-Phe(4-Cl)-Arg was synthesized by standard solid phase peptide synthesis methods. Using appropriate Fmoc protected amino acids, the method described in Example 1 afforded Fmoc-Ser(Bzl)-D-Phe(4-Cl)-Arg-Resin. The Fmoc group was removed and the resin treated with acetic anhydride/pyridine to introduce an acetyl group at the N-terminus. The peptide was cleaved from the resin by its treatment with a mixture of 50% TFA—2.5% TIS and 2.5% water in DCM for 1 hour. The final product was precipitated by adding cold ether and collected by filtration. Final purification was by RP-HPLC using a C-18 column.

The peptide is a linear peptide with a free acid at the C-terminus and an acetyl group at the N-terminus of the formula:

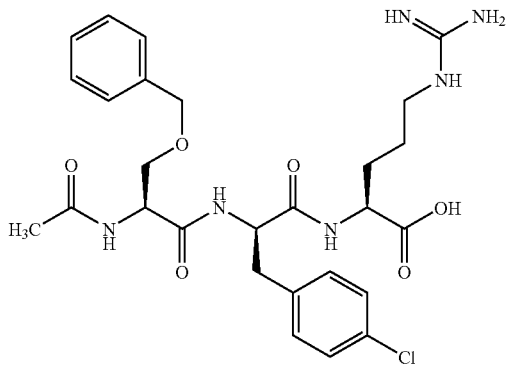

The peptide has a net molecular weight of 575, and was obtained as a trifluoroacetate salt.

Example 14

Binding of Peptides to Melanocortin Receptors

The binding of the peptides of Examples 1 to 13, inclusive, to melanocortin receptors was evaluated, with results shown on Table 1. Relative binding was determined by competitive inhibition using an α-MSH analog, iodinated NDP-MSH. B16-F1 mouse melanoma cells were used as the source of MC1 receptors and HEK 293 cells, transfected with human melanocortin receptor sequences, were used as the source of MC3, MC4 and MC5 receptors. A standard competitive binding assay protocol as described above was followed, using $^{125}$I-NDP-MSH as the radioligand. A "0" percent inhibition was assigned when the raw percent inhibition, as an average of at least triplicate measures, was between −10% and 10%; in the majority of instances, the raw percent inhibition was between −10% and 0% inhibition.

TABLE 1

| Peptide | % Inhibition at 10 μM concentration at MC1-, 3-, 4- and 5-Receptors |
|---|---|
| $NH_2$—$(CH_2)_6$—CO-Ser(Bzl)-D-Phe(4-Cl)-Arg | 0 |
| $NH_2$—$(CH_2)_6$—CO-Ser(Bzl)-D-Phe(4-Cl)-Arg-$NH_2$ | 0 |
| $NH_2$—$(CH_2)_6$—CO-Ser(Bzl)-D-Nal 2-Arg | 0 |
| $NH_2$—$(CH_2)_6$—CO-Ser(Bzl)-D-Nal 2-Arg-$NH_2$ | 0 |
| $NH_2$—$(CH_2)_6$—CO-Ser(Bzl)-D-Phe(4-Cl)-Arg($NO_2$) | 0 |
| $NH_2$—$(CH_2)_6$—CO-Ser(Bzl)-D-Phe(4-Cl)-Cit | 0 |
| $NH_2$—$(CH_2)_6$—CO-Ser(Bzl)-D-Phe(4-Cl)-Lys | 0 |
| $NH_2$—$(CH_2)_6$—CO-Ser(Bzl)-D-Phe(4-Cl)-Orn | 0 |
| $NH_2$—$(CH_2)_6$—CO-Ser(Bzl)-D-Phe(4-Cl)-Ala | 0 |
| $NH_2$—$(CH_2)_6$—CO-Ser(Bzl)-D-Ala-Arg | 0 |
| $NH_2$—$(CH_2)_6$—CO-Ala-D-Phe(4-Cl)-Arg | 0 |
| Ser(Bzl)-D-Phe(4-Cl)-Arg | 0 |
| Ac-Ser(Bzl)-D-Phe(4-Cl)-Arg | 0 |

Example 15

Determination of Induction of Penile Erections

The ability of the peptides of Examples 1 to 13 to induce penile erection in male rats was evaluated. Male Sprague-Dawley rats weighing 200-250 g were kept on a 12 hour on/off light cycle with food and water ad libitum. All behavioral studies were performed between 10 a.m. and 5 p.m. Groups of 4-8 rats were treated with peptides at a variety of doses via intravenous administration. Immediately after administration, rats were placed into individual polystyrene cages (27 cm long, 16 cm wide, and 25 cm high) for behavioral observation. Rats were observed for 30 minutes and the number of yawns, grooming bouts and penile erections were recorded in three 10-minute bins. Each of the peptides of Examples 1 to 13 was observed to positively induce penile erections in male rats by intravenous injection at one or more dose levels, using saline as a control, with results scored positive where the difference in observed penile erections was statistically relevant.

Example 16

Induction of Penile Erections with $NH_2$—$(CH_2)_6$CO-Ser(Bzl)-D-Phe(4-Cl)-Arg

The efficacious dose of $NH_2$—$(CH_2)_6$CO-Ser(Bzl)-D-Phe (4-Cl)-Arg, made as in Example 1 above, to induce penile erection in Sprague Dawley rats by intravenous dosing and oral administration was determined. Male Sprague Dawley rats were administered NH$_2$(CH$_2$)$_6$CO-Ser(Bzl)-D-Phe(4-Cl)-Arg, in various doses and utilizing intravenous and oral routes of administration, with appropriate controls, as in Example 15, and were observed for erections and side effects, including excessive grooming, yawning, vacuous chewing, hypoactivity, and heaving. NH$_2$—(CH$_2$)$_6$CO-Ser(Bzl)-D-Phe(4-Cl)-Arg was efficacious at doses as low as 0.1 to 1 μg/kg of body weight when administered by oral means, and at doses lower than 0.001 μg/kg of body weight when administered by intravenous means.

Example 17

Induction of Penile Erections Using NH$_2$—(CH$_2$)$_6$—CO-Ser(Bzl)-D-Phe(4-Cl)-Arg(NO$_2$) by Intravenous Dosing The efficacious dose of NH$_2$—(CH$_2$)$_6$—CO-Ser(Bzl)-D-Phe(4-Cl)-Arg(NO$_2$), made as in Example 5 above, to induce penile erection in Sprague Dawley rats by intravenous dosing was determined. Male Sprague Dawley rats were administered NH$_2$—(CH$_2$)$_6$—CO-Ser(Bzl)-D-Phe(4-Cl)-Arg(NO$_2$), in various doses and utilizing different routes of administration, with appropriate controls, as in Example 15, and were observed for erections and side effects, including excessive grooming, yawning, vacuous chewing, hypoactivity, and heaving. It was determined that NH$_2$—(CH$_2$)$_6$—CO-Ser(Bzl)-D-Phe(4-Cl)-Arg(NO$_2$) was efficacious at doses as low as 0.001 to 10 μg/kg of body weight when administered by intravenous means, with efficacy determined by induction of penile erection in 100% of animals. The optimal dose response was at 1 μg/kg of body weight. FIG. 1 depicts the dose response profile, with the error bars depicting standard deviation where n (the number of animals) is between 8 and 19, depending on the dose point.

Example 18

Induction of Penile Erections Using NH$_2$—(CH$_2$)$_6$—CO-Ser(Bzl)-D-Phe(4-Cl)-Arg(NO$_2$) by Intranasal Administration The efficacious dose of NH$_2$—(CH$_2$)$_6$—CO-Ser(Bzl)-D-Phe(4-Cl)-Arg(NO$_2$), made as in Example 5 above, to induce penile erection in Sprague Dawley rats by intranasal administration using a micropipetor to deliver 25 μL of solution into one nostril was determined. Male Sprague Dawley rats were administered NH$_2$—(CH$_2$)$_6$—CO-Ser(Bzl)-D-Phe(4-Cl)-Arg(NO$_2$), in various doses by intranasal administration, with appropriate controls, and were observed for erections and side effects, including excessive grooming, yawning, vacuous chewing, hypoactivity, and heaving. It was determined that NH$_2$—(CH$_2$)$_6$—CO-Ser(Bzl)-D-Phe(4-Cl)-Arg(NO$_2$) was efficacious at doses between 0.01 μg/kg and 100 μg/kg of body weight when administered by intranasal means. The peak dose response was at an intranasal dose of 0.1 μg/kg of body weight.

Example 19

Induced Penile Erections Not Inhibited by MCR-R Antagonist

It is known that MC4-R antagonists inhibit the erectile activity of MC4-R agonists in a dose dependent manner. Such antagonists include SHU9119, a nonselective melanocortin antagonist of the formula Ac-Nle-cyc/o(-Asp-His-D-Nal(2')-Arg-Trp-Lys)-NH$_2$ (Hruby V. J., Lu D., Sharma S. D., et al. Cyclic lactam alpha-melanotropin analogues of Ac-Nle$^4$-cyclo[Asp$^5$, D-Phe$^7$, Lys$^{10}$]-NH$_2$ with bulky aromatic amino acids at position 7 show high antagonist potency and selectivity at specific melanocortin receptors. *J Med Chem* 38:3454-3461 (1995)). Antagonists such as SHU9119 are known to inhibit MT-II and other known melanocortin receptor-specific agonists that induce erectile activity. SHU9119 was administered to male rats approximately 5 minutes before administration of either NH$_2$—(CH$_2$)$_6$CO-Ser(Bzl)-D-Phe(4-Cl)-Arg or NH$_2$—(CH$_2$)$_6$CO-Ser(Bzl)-D-Phe(4-Cl)-Arg-Trp-NH$_2$, with Ac-Nle-cyc/o(Asp-His-D-Phe-Arg-Trp-Lys)-OH, a known MC4-R agonist, as a positive control. Neither NH$_2$—(CH$_2$)$_6$CO-Ser(Bzl)-D-Phe(4-Cl)-Arg nor NH$_2$—(CH$_2$)$_6$CO-Ser(Bzl)-D-Phe(4-Cl)-Arg-Trp-NH$_2$ was inhibited by administration of SHU9119, and both resulted in erections at a rate equivalent to that obtained without pre-administration of SHU9119. The peptide Ac-Nle-cyc/o(Asp-His-D-Phe-Arg-Trp-Lys)-OH, disclosed in U.S. Pat. No. 6,579,968, used as a positive control, was inhibited by SHU9119.

Example 20

Melanocortin Receptor-Specific Functional Activity Assay

Stimulation of intracellular CAMP production by each of the peptides of Examples 1 to 13, inclusive, was determined utilizing transfected HEK-293 cells expressing hMC4-R, notwithstanding that none of the peptides had been found to bind MC4-R at a 10 μM concentration. A standard CAMP stimulation and measurement protocol as described above was followed. None of the peptides exhibited any stimulation of intracellular CAMP, while in parallel experiment NDP acting as positive control for stimulation of MC4-R caused production and accumulation of intracellular CAMP.

Example 21

Receptor Specificity Screening

The peptide NH$_2$—(CH$_2$)$_6$CO-Ser(Bzl)-D-Phe(4-Cl)-Arg was tested at 10 μM concentration for binding to a panel of known central and peripheral receptors and neurotransmitters, including steroid receptors, neurotransmitter receptors, brain/gut peptide receptors, growth factor/hormone receptors and other receptors, and for interaction with a panel of known ion channels and enzymes systems. No binding or activity with NH$_2$—(CH$_2$)$_6$CO-Ser(Bzl)-D-Phe(4-Cl)-Arg was detected with any panel members.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An isolated peptide or a pharmaceutically acceptable salt thereof of the formula:
$NH_2$—$(CH_2)_6$—CO-Ser(Bzl)-D-Phe(4-Cl)-Arg,
$NH_2$—$(CH_2)_6$—CO-Ser(Bzl)-D-Phe(4-Cl)-Arg-$NH_2$,
$NH_2$—$(CH_2)_6$—CO-Ser(Bzl)-D-Nal 2-Arg,
$NH_2$—$(CH_2)_6$—CO-Ser(Bzl)-D-Nal 2-Arg-$NH_2$,
$NH_2$—$(CH_2)_6$—CO-Ser(Bzl)-D-Phe(4-Cl)-Arg($NO_2$),
$NH_2$—$(CH_2)_6$—CO-Ser(Bzl)-D-Phe(4-Cl)-Cit,
$NH_2$—$(CH_2)_6$—CO-Ser(Bzl)-D-Phe(4-Cl)-Lys,
$NH_2$—$(CH_2)_6$—CO-Ser(Bzl)-D-Phe(4-Cl)-Orn,
$NH_2$—$(CH_2)_6$—CO-Ser(Bzl)-D-Phe(4-Cl)-Ala,
$NH_2$—$(CH_2)_6$—CO-Ala-D-Phe(4-Cl)-Arg,
$NH_2$—$(CH_2)_6$—CO-Ser(Bzl)-D-Ala-Arg
Ser(Bzl)-D-Phe(4-Cl)-Arg, or
Ac-Ser(Bzl)-D-Phe(4-Cl)-Arg.

2. A pharmaceutical composition for treating sexual dysfunction in a mammal, comprising a peptide or pharmaceutically acceptable salt thereof of claim 1 and a pharmaceutically acceptable carrier.

3. The pharmaceutical composition of claim 2, further comprising a second sexual dysfunction pharmaceutical agent.

4. The pharmaceutical composition of claim 2, wherein the second sexual dysfunction pharmaceutical agent is an MC4-R agonist or a PDE-5 inhibitor.

* * * * *